(12) United States Patent
Way et al.

(10) Patent No.: US 10,905,663 B2
(45) Date of Patent: Feb. 2, 2021

(54) TREATMENT OF DEMYELINATING DISORDERS

(71) Applicant: THE UNIVERSITY OF CHICAGO, Chicago, IL (US)

(72) Inventors: Sharon Way, Chicago, IL (US); Benjamin Clayton, Chicago, IL (US); Brian Popko, Monee, IL (US)

(73) Assignee: The University of Chicago, Chicago, IL (US)

( * ) Notice: Subject to any disclaimer, the term of this patent is extended or adjusted under 35 U.S.C. 154(b) by 324 days.

(21) Appl. No.: 14/773,088

(22) PCT Filed: Mar. 5, 2014

(86) PCT No.: PCT/US2014/020896
§ 371 (c)(1),
(2) Date: Sep. 4, 2015

(87) PCT Pub. No.: WO2014/138298
PCT Pub. Date: Sep. 12, 2014

(65) Prior Publication Data
US 2016/0015659 A1    Jan. 21, 2016

Related U.S. Application Data

(60) Provisional application No. 61/772,875, filed on Mar. 5, 2013.

(51) Int. Cl.
*A61K 31/155*    (2006.01)
*A61K 31/136*    (2006.01)
(Continued)

(52) U.S. Cl.
CPC .......... *A61K 31/155* (2013.01); *A61K 9/0019* (2013.01); *A61K 31/136* (2013.01);
(Continued)

(58) Field of Classification Search
None
See application file for complete search history.

(56) References Cited

U.S. PATENT DOCUMENTS

| 7,932,422 B2 | 4/2011 | Bertolotti et al. | 564/227 |
| 2008/0131483 A1 | 6/2008 | Abdulrazik | 424/427 |

(Continued)

FOREIGN PATENT DOCUMENTS

| WO | WO 1995/001096 | 1/1995 |
| WO | WO 2011/019845 | 2/2011 |

(Continued)

OTHER PUBLICATIONS

'T Hart, et al., Modelling of multiple sclerosis: lessons learned in a non-human primate, Oct. 2004, Lancet Neurol vol. 3:588-597.*

(Continued)

*Primary Examiner* — John D Ulm
(74) *Attorney, Agent, or Firm* — Norton Rose Fulbright US LLP

(57) ABSTRACT

This invention discloses methods and compositions for the treatment of demyelinating disorders. Specifically, the invention relates to the use guanabenz or guanabenz derivative for treating demyelinating disorders.

17 Claims, 15 Drawing Sheets

(51) Int. Cl.
    *A61K 31/137*     (2006.01)
    *A61K 31/225*     (2006.01)
    *A61K 31/277*     (2006.01)
    *A61K 31/4409*     (2006.01)
    *A61K 38/21*     (2006.01)
    *A61K 9/00*     (2006.01)
    *A61K 38/03*     (2006.01)
    *A61K 39/395*     (2006.01)
    *A61K 45/06*     (2006.01)
    *A61K 39/00*     (2006.01)

(52) U.S. Cl.
    CPC .......... *A61K 31/137* (2013.01); *A61K 31/225* (2013.01); *A61K 31/277* (2013.01); *A61K 31/4409* (2013.01); *A61K 38/03* (2013.01); *A61K 38/215* (2013.01); *A61K 39/3955* (2013.01); *A61K 45/06* (2013.01); *A61K 2039/505* (2013.01)

(56) References Cited

U.S. PATENT DOCUMENTS

| | | | |
|---|---|---|---|
| 2009/0227646 A1 | 9/2009 | Davis et al. | 514/381 |
| 2010/0172869 A1 | 7/2010 | Masuoka | 424/85.6 |
| 2012/0196931 A1 | 8/2012 | Lukashev et al. | 514/547 |
| 2012/0225070 A1 | 9/2012 | Smith et al. | 424/135.1 |

FOREIGN PATENT DOCUMENTS

| | | |
|---|---|---|
| WO | WO 2012112933 | 8/2012 |
| WO | WO 2014108520 | 7/2014 |

OTHER PUBLICATIONS

Wekerle et al., Animal models of multiple sclerosis, 2006, Drug Discovery Today: Disease Models 3(4):359-367.*
Ransohoff, R. M., Animal models of multiple sclerosis: the good, the bad and the bottom line, Aug. 2012, Nature Neuroscience 15(8):1074-1077.*
Behan et al., the sad plight of multiple sclerosis research (low on fact, high on fiction): critical data to support it being a neurocristopathy, 2010, Inflammopharmacology 18:265-290.*
International Search Report and Written Opinion issued in PCT/US14/20896, dated Jun. 10, 2014.
Constantinescu et al, *British Journal of Pharmacology* 164 (2011): 1079-1106.
Robinson et al., *Handb. Clin. Neurol.* 122 (2014): 173-189.
Constantinescu et al., *British Journal of Pharmacology* 164, 1079-1106, 2011.
Maier et al., *The American Journal of Pathology* 169:4, 1353-1364, 2006.
Steinman et al., *TRENDS in Immunology* 26:11, 565-571, 2005.

* cited by examiner

TREATMENT OF DEMYELINATING DISORDERS

CROSS-REFERENCE TO RELATED APPLICATIONS

This application is a national phase application under 35 U.S.C. § 371 of International Application No. PCT/US2014/020896, filed Mar. 5, 2014, which claims the benefit of U.S. Provisional Application No. 61/772,875, filed on Mar. 5, 2013. The entire contents of each of the above-referenced disclosures are specifically incorporated herein by reference without disclaimer.

STATEMENT AS TO FEDERALLY SPONSORED RESEARCH

This invention was made with government support under NS034939, awarded by the National Institutes of Health. The government has certain rights in the invention.

BACKGROUND OF THE INVENTION

Demyelinating disorders affect more than 2.5 million people worldwide. A demyelinating disorder is a condition in which the myelin sheath of a neuronal cell is damaged. Myelin is an electrically insulating material that forms layers, or myelin sheaths, around neuronal axons. Myelin serves many functions and is essential for nervous system function. One of the central functions of myelin is to increase the speed of electrical impulses along an axon, another function is to prevent electrical current from dissipating from the axon. Myelin is produced by two cell types: oligodendrocytes and Schwann cells. Oligodendrocytes are glial cells that supply myelin to neurons of the central nervous system, Schwann cells provide myelin to peripheral neurons. Demyelination results in impaired transmission of neuronal impulses, resulting in diverse symptoms that possibly include motor impairments, sensory impairments, cognitive dysfunction, emotional disturbances, and impaired coordination.

There are many demyelinating disorders, the most common of which is multiple sclerosis. Multiple sclerosis (MS) is an autoimmune disease affecting the brain and spinal cord, in which the body's own immune system attacks myelin or myelin producing cells. Although MS symptoms vary widely, one of the pathological hallmarks of MS is the presence of multiple demyelinated plaques in the CNS. Demyelinated plaques are associated with blood-brain-barrier (BBB) breakdown, inflammation, demyelination, and axonal degeneration. BBB breakdown allows for the infiltration of autoreactive cytokines that attack myelin and myelin associated proteins such as myelin oligodendrocyte glycoprotein (MOG), proteolipid protein (PLP), or myelin basic protein (MBP), among others. In MS, early neurologic dysfunction is related to demyelination that results in slowed or blocked conductance of electrical signals. Most subjects suffering from MS exhibit a relapsing/remitting form of the disease, which is characterized by discontinuous bouts of clinical symptoms (relapse) punctuated be periods of symptomatic relief (remission). Other subjects experience chronic, progressive MS, wherein symptoms worsen over time without periods of symptomatic relief Some subjects experience relapsing/remitting MS early in the course of the disease but then eventually transition to a chronic, progressive form of the disease. Besides MS, other common demyelinating disorders include but are not limited to acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, diffuse white matter injury, Guillain-Barré Syndrome, central pontine myelinolysis, inherited demyelinating diseases such as leukodystrophy, and Charcot Marie Tooth Disease. Sufferers of pernicious anemia or Vitamin B12 deficiency can also suffer nerve damage if the condition is not diagnosed quickly.

The precise etiologies of many CNS disorders, including demyelinating disorders, are not fully characterized. Recent studies have implicated endoplasmic reticulum (ER) stress response pathways in several CNS disorders (J Cell Mol. Med. 2011 October; 15(10):2025-39). ER stress is a highly evolutionarily conserved pathway that serves to reduce the burden of misfolded or unfolded proteins in the ER. Even a modest accumulation of unfolded/misfolded proteins in the ER can induce ER stress, compromising the ability of the ER to properly process secretory and/or membrane proteins. The ER stress response pathway involves three main signaling pathways, the IRE1 pathway, the ATF6 pathway, and the PERK pathway. Each of these pathways function to reduce ER burden and promote cell survival, but may also ultimately result in cell death in cases of persistent ER stress (Physiology 22:193-201, 2007). In particular, the PERK pathway has been implicated in demyelinating disorders such as MS. The PERK pathway leads to phosphorylation of eukaryotic initiation factor 2-alpha (eIF2α), which has the main effects of globally suppressing protein translation and selectively promoting translation of the transcription factor ATF4, which in turn activates a number of target genes, including amino acid transporters and cellular redox genes (Physiology 22:193-201, 2007). The global suppression of protein translation serves to reduce the burden of misfolded/unfolded proteins in the ER (Physiology 22:193-201, 2007).

Guanabenz is a small molecule guanidine derivative. It is known to be an $\alpha_2$-adrenergic agonist, although it may also exert biological effects through other mechanisms. Guanabenz is administered to treat hypertension. The antihypertensive effects are thought to be mediated by its $\alpha_2$-adrenergic agonist activity, resulting in reduced sympathetic stimulation of the heart, kidneys, and peripheral vasculature, and reduced blood pressure and pulse rate. Guanabenz is typically administered twice a day as an oral tablet formulation. It has been reported that guanabenz can impair memory function (Behav. Brain Res. 2004 Aug. 31; 153(2):409-17) and reduce hippocampal neurogenesis (J Neurosci. 2010 Jan. 20; 30(3):1096-109). However, the use of guanabenz or its derivatives for the treatment of demyelinating disorders has not been reported. A study by Tsaytler et al (Science 2011 Apr. 1; 332(6025):91-4) implies that guanabenz reduces ER stress burden, by reducing stress-induced dephosphorylation of eIF2α. However, this study is limited to in vitro cell culture of epithelial cells. No in vivo data is provided, nor is there any hint for the in vivo use of guanabenz in treating any demyelinating disorders.

Presently, there are no known cures for demyelinating disorders, including multiple sclerosis. There are several drugs approved by the FDA for multiple sclerosis, however, these only provide some limited symptomatic relief. In fact, several of the currently approved treatments for demyelinating disorders are associated with significant adverse effects, such as flu-like symptoms, fever, liver damage, and in some cases, significantly increased risk for progressive multifocal leukoencephalopathy. Therefore, there is a pressing need for improved therapies for demyelinating disorders.

SUMMARY OF THE INVENTION

Accordingly, the present invention provides methods and compositions that address the limitations of current therapeutics for a variety of demyelinating disorders.

In one aspect, the present invention provides a method of increasing viability of a neuronal cell in a subject suffering from a demyelinating disorder, comprising administering to the subject suffering from a demyelinating disorder an effective amount of a compound of Formula I (below):

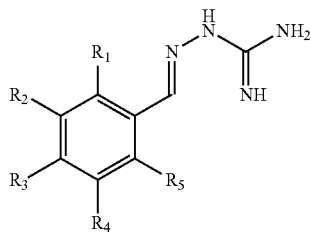

Formula I or derivative or pharmaceutically acceptable salt thereof, wherein $R_1$, $R_2$, $R_3$, $R_4$, and $R_5$ are independently hydrogen, deuterium, halogen, haloalkyl, alkyl, alkoxy, hydroxyl, aryl, or aryloxy, thereby increasing viability of a neuronal cell in said subject.

In another aspect, the present invention provides a method of treating a symptom of a demyelinating disorder, comprising the step of administering to a subject in need thereof an effective amount of a compound of Formula I, thereby treating a symptom of a demyelinating disorder in said subject.

In another aspect, the present invention provides a method of delaying onset of a symptom of a demyelinating disorder in a subject at risk of the demyelinating disorder, comprising administering to the subject at risk of a demyelinating disorder an effective amount of a compound of Formula I, thereby delaying onset of a symptom of a demyelinating disorder in the subject.

In another aspect, the present invention provides a method of reducing relapse and/or severity of a symptom of a demyelinating disorder in a subject suffering from the demyelinating disorder, comprising administering to the subject at suffering from the demyelinating disorder an effective amount of a compound of Formula I, thereby reducing relapse and/or severity of a symptom of a demyelinating disorder in the subject.

In another aspect, the present invention provides a method of increasing viability of cells of the oligodendrocyte lineage when exposed to an inflammatory agent, comprising administering to the cells of the oligodendrocyte lineage with an amount of a compound of Formula I, effective in reducing apoptosis of said cells of the oligodendrocyte lineage, wherein said apoptosis is induced by said inflammatory agent, thereby increasing viability of the cells of the oligodendrocyte lineage.

In another aspect, the present invention provides a method of protecting a brain cell from inflammation in a subject in need thereof, the method comprising administering to the subject an effective amount of a compound of Formula I, thereby protecting a brain cell from inflammation in the subject. In some embodiments, the subject has or is suspected of having amyotrophic lateral sclerosis (ALS).

In some aspects embodiments of the compound of Formula I described herein, $R_1$ and $R_5$ are not hydrogen.

In some aspects embodiments of the compound of Formula I described herein, $R_1$ and $R_5$ are halogen.

In some aspects embodiments of the compound of Formula I, the compound is of Formula II (below) or derivative or pharmaceutically acceptable salt thereof:

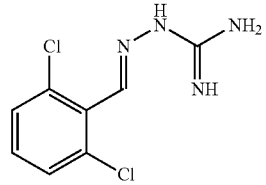

Formula II

In some embodiments of the present invention, the demyelinating disorder is multiple sclerosis.

In other embodiments of the present invention, the demyelinating disorder is selected from the group consisting of: acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, Guillain-Barré Syndrome, central pontine myelinolysis, diffuse white matter injury, inherited demyelinating diseases such as leukodystrophy, and Charcot Marie Tooth Disease.

In some embodiments, the symptom of a demyelinating disorder is selected from the group consisting of: fatigue, somatosensory dysfunction, tingling, pain, numbness, balance problems, problems with walking, changes in vision, depression, emotional changes, mood swings, impaired cognition, muscle dysfunction, impaired muscle coordination, sexual impairment, speech impairment, swallowing impairment, bladder dysfunction, bowel dysfunction.

In some embodiments of the invention, about 1 mg to about 64 mg of the compound is administered to the subject.

In other embodiments of the invention, about 4 mg to about 20 mg of the compound is administered to the subject.

In still yet others embodiment of the present invention, the compound is administered orally.

In some embodiments, the brain cell is a neuronal cell. In other embodiments, the brain cell is a glial cell. In still yet other embodiments, the brain cell is a cell of the oligodendrocyte lineage.

In some embodiments, the neuronal cell is a neuron.

In some aspects of the invention, administration of said compound substantially obviate relapse of a symptom of a demyelinating disorder in a subject over a course of at least 1 month.

In some embodiments of the invention, the compound of Formula I is a compound of Formula II, wherein upon administering an effective amount yields a reduction in apoptosis by at least 20%.

In other aspects of the invention, administration of said compound reduces severity of a symptom of a demyelinating disorder in a subject by at least about 50%.

In some aspects, the present invention provides an oral dosage form comprising a unit dosage of guanabenz present in an amount effective in ameliorating a symptom of a demyelinating disorder, wherein the oral dosage form comprises instructions for use of said dosage form for a subject suffering from said demyelinating disorder. In some embodiments of the oral dosage form, the instructions specify administering the unit dosage according to a regime having at least one dose per day.

In some cases, this disclosure provides an oral dosage form comprising about 64 mg of a compound provided herein, such as guanabenz.

In some cases, administration of a compound provided in this disclosure is combined with at least one another agent. In some embodiments, the at least one other agent is useful for the treatment of a demyelinating disorder. In some embodiments, the at least one other agent is glatiramer acetate. In some cases, guanabenz and glatiramer acetate are both administered to a subject. In some cases, about 64 mg of guanabenz is administered to a subject receiving glatiramer acetate. In some embodiments, the at least one other agent is interferon-beta. In some embodiments, the at least one other agent is interferon beta-1a. In some cases, guanabenz and interferon beta-1a are both administered to a subject. In some cases, about 64 mg of guanabenz is administered to a subject receiving interferon beta-1a. In some embodiments, the at least one other agent is interferon beta-1b. In some cases, guanabenz and interferon beta-1b are both administered to a subject. In some cases, about 64 mg of guanabenz is administered to a subject receiving interferon beta-1b. In some embodiments, the at least one other agent is dimethyl fumarate (BG-12). In some cases, guanabenz and dimethyl fumarate are both administered to a subject. In some cases, about 64 mg of guanabenz is administered to a subject receiving dimethyl fumarate. In some embodiments, the at least one other agent is fingolimod (FTY720). In some cases, guanabenz and fingolimod are both administered to a subject. In some cases, about 64 mg of guanabenz is administered to a subject receiving fingolimod. In some embodiments, the at least one other agent is mitoxantrone. In some cases, guanabenz and mitoxantrone are both administered to a subject. In some cases, about 64 mg of guanabenz is administered to a subject receiving mitoxantrone. In some embodiments, the at least one other agent is natalizumab. In some cases, guanabenz and natalizumab are both administered to a subject. In some cases, about 64 mg of guanabenz is administered to a subject receiving natalizumab. In some embodiments, the at least one other agent is dalfampridine. In some cases, guanabenz and dalfampridine are both administered to a subject. In some cases, about 64 mg of guanabenz is administered to a subject receiving dalfampridine. In some embodiments, the at least one other agent is teriflunomide. In some cases, guanabenz and teriflunomide are both administered to a subject. In some cases, about 64 mg of guanabenz is administered to a subject receiving teriflunomide. In some embodiments, the at least one other agent is daclizumab. In some cases, guanabenz and daclizumab are both administered to a subject. In some cases, about 64 mg of guanabenz is administered to a subject receiving daclizumab.

In some cases, the 64 mg of guanabenz is administered in a single dose. In some cases, the single dose is administered to the subject in the evening.

In some cases, this disclosure provides a composition comprising a compound provided herein and an additional therapeutic agent. In some embodiments, the additional therapeutic agent is an agent useful for the treatment of a demyelinating disorder. In some embodiments, the additional therapeutic agent is glatiramer acetate. In some embodiments, the additional therapeutic agent is dimethyl fumarate (BG-12). In some embodiments, the additional therapeutic agent is dimethyl fumarate (BG-12). In some embodiments, the additional therapeutic agent is fingolimod (FTY720). In some embodiments, the additional therapeutic agent is interferon beta-1a. In some embodiments, the additional therapeutic agent is interferon beta-1b. In some embodiments, the additional therapeutic agent is mitoxantrone. In some embodiments, the additional therapeutic agent is natalizumab. In some embodiments, the additional therapeutic agent is dalfampridine. In some embodiments, the additional therapeutic agent is teriflunomide. In some embodiments, the additional therapeutic agent is daclizumab. In some cases, the compound is guanabenz. In some cases, the composition comprises a pharmaceutically acceptable carrier. In some cases, the pharmaceutically acceptable carrier is suitable for injection. In some cases, the injection is a subcutaneous injection. In some cases, the injection is intravenous administration.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Overview

Figure 1:
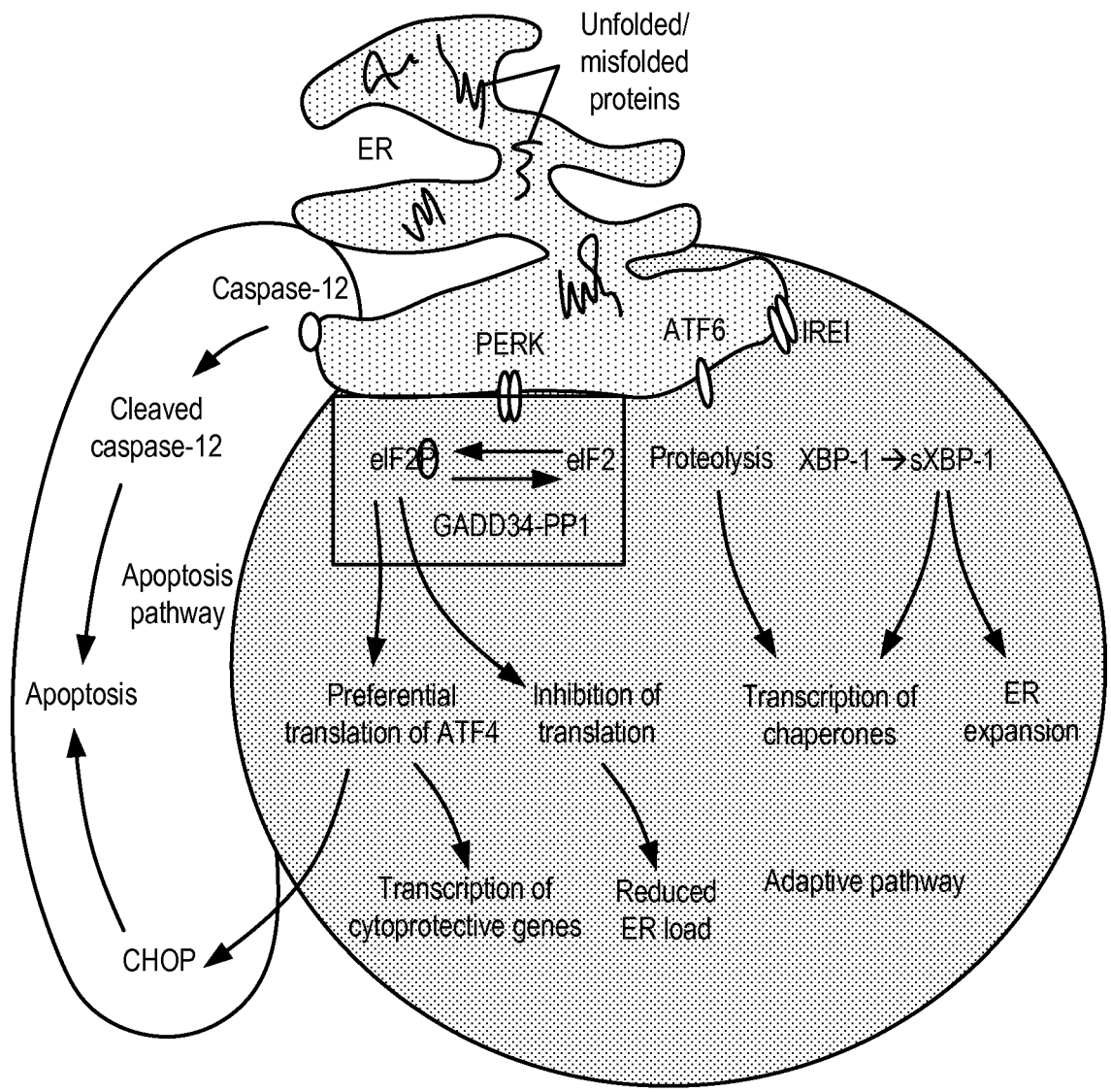
FIG. 1 illustrates the canonical ER stress response pathway. The red box indicates the pathway modulated by Guanabenz, resulting in decreased GADD34-PP1 activity and reduced eIF2α dephosphorylation.

In general, described below are methods and compositions for the use of guanabenz or guanabenz derivatives for the treatment of demyelinating disorders, including but not limited to multiple sclerosis. Disclosed herein are a number of methods for the use of guanabenz or guanabenz derivatives for the treatment of, for ameliorating the symptoms of, for delaying onset of symptoms of, or for reducing relapse severity of demyelinating disorders. Also disclosed are methods for the use of guanabenz or guanabenz derivatives to provide neuroprotection to a subject in need thereof. In some embodiments the subject is suffering from a demyelinating disorder. In some embodiments the subject is suffering from or is suspected of having Amyotrophic lateral sclerosis (ALS). Furthermore, disclosed herein are methods for the use of guanabenz or guanabenz derivatives to provide protection of cells of the oligodendrocyte lineage, the cells providing the myelin sheath in the central nervous system, wherein the cells of the oligodendrocyte lineage may suffer damage, stress, or death due to inflammatory insult. Also disclosed is a composition for an oral dosing package, comprising instructions for use of said dosage form for a subject suffering from a demyelinating disorder.

DEFINITIONS

As used in the specification and claims, the singular form "a", "an" and "the" include plural references unless the context clearly dictates otherwise. For example, the term "a symptom" may include a plurality of symptoms.

The term "about" means within an acceptable error range for the particular value as determined by one of ordinary skill in the art. In some cases, the acceptable error range may depend in part on the limitations of the measurement system. For example, "about" can mean within 1 or more than 1 standard deviation, per the practice in the art. Alternatively, "about" can mean a range of up to 25%, preferably up to 10%, more preferably up to 5%, and more preferably still up to 1% of a given value. Alternatively, the term can mean within an order of magnitude, preferably within 10-fold, preferably within 5-fold, and more preferably within 2-fold, of a value. Where particular values are described in the application and claims, unless otherwise stated the term "about" meaning within an acceptable error range for the particular value should be assumed.

For the purposes of this invention, a "demyelinating disorder" is any condition involving dysfunction of the myelin sheath encasing neuronal axons. Examples of demyelinating disorders include but are not limited to multiple sclerosis, acute disseminated encephalomyelitis, periventricular leukomalacia, periventricular white matter injury, Tabes Dorsalis, Devic's disease, Optic neuritis, progressive multifocal leukoencephalopathy, transverse myelitis, chronic inflammatory demyelinating polyneuropathy, anti-MAG peripheral neuropathy, Adrenoleukodystrophy, adrenomyeloneuropathy, Guillain-Barré Syndrome, central pontine myelinolysis, diffuse white matter injury, inherited demyelinating diseases such as demyelinating leukodystrophies, and Charcot Marie Tooth Disease. In some embodiments, the demyelinating disorder can be the result of pernicious anemia or vitamin B12 deficiency.

The terms "treating" or "treating a symptom of" a demyelinating disorder are used interchangeably. These terms refer to, but are not limited to, utilizing a method or methods to achieve a therapeutic benefit and/or a prophylactic benefit. In some cases, a therapeutic benefit may refer to reducing the severity of a symptom or symptoms of a demyelinating disorder. In some cases, a therapeutic benefit may refer to addressing or correcting the biological mechanisms underlying the demyelinating disorder. In other cases, a therapeutic benefit may refer to halting or slowing the progression of a demyelinating disorder. In other cases, a therapeutic benefit may refer to reducing demyelination or to promoting remyelination. In yet other cases, a therapeutic benefit may refer to reducing inflammation associated with a number of demyelinating disorders. In yet other cases, a therapeutic benefit may refer to protecting brain cells from inflammation associated with a number of demyelinating disorders. In yet other cases, a therapeutic benefit may refer to reducing the size and/or number of white matter plaques and/or lesions. In still yet other cases, a therapeutic benefit may refer to increasing the viability and/or health of cells of the oligodendrocyte lineage. In still yet other cases, therapeutic benefit may refer to providing neuroprotection of axons. In addition, a prophylactic benefit may refer to reducing the risk of developing a demyelinating disorder. In some cases, a prophylactic benefit may refer to delaying the onset of symptom(s) of a demyelinating disorder. In some cases, a prophylactic benefit may refer to reducing or delaying relapse of a demyelinating disorder.

In the present invention, "the treatment" can involve administering to a subject a therapeutically effective amount of guanabenz or a guanabenz derivative. In some embodiments, the composition comprises a pharmaceutically acceptable carrier. In some embodiments, the administration of guanabenz or guanabenz derivative may involve co-administration with another therapeutic agent for the treatment of a demyelinating disorder, including, but not limited to, glatiramer acetate, dimethyl fumerate (BG-12), fingolimod (FTY720), interferon beta-1a, interferon beta-1b, mitoxantrone, natalizumab, dalfampridine, teriflunomide, or daclizumab.

The terms "co-administration," "administered in combination with", "combination therapy" and their grammatical equivalents, encompass administration of two or more agents, one of which comprises the compound(s) disclosed in the present invention, to a subject so that the agents and/or their metabolites are present in the animal at the same time. Co-administration may involve simultaneous administration in separate compositions, or may involve administration at different times in separate compositions, or may involve administration in a single composition in which the agents are present. Co-administered agents may be in the same formulation. Co-administered agents may also be in different formulations.

"An effective amount" and "a therapeutically effective amount" are used interchangeably. "An effective amount" is an amount of the composition that achieves a therapeutic benefit and/or prophylactic benefit. The therapeutically effective amount can be determined by a physician or one of ordinary skill in the art. One of ordinary skill in the art will understand that an effective amount may vary from subject to subject, depending on the subject's size, age, general health, route of administration, the subject's level of risk for developing a demyelinating disorder, the subject's severity of symptom(s), the subject's progression of the disorder, or other factors. One of ordinary skill in the art will understand that an effective amount for a particular subject may change over time, depending on factors described above.

A "sub-therapeutic amount" of an agent is an amount less than the effective amount for that agent. When combined with an effective or sub-therapeutic amount of one or more additional agents, the sub-therapeutic amount can produce a result desired by the physician, due to, for example, synergy in the resulting efficacious effects, or reduced adverse effects.

A "synergistically effective" therapeutic amount or "synergistically effective" amount of an agent or therapy is an amount which, when combined with an effective or sub-therapeutic amount of one or more additional agents, produces a greater effect than when either of the agents are used alone. In some embodiments, a synergistically effective therapeutic amount of an agent or therapy produces a greater effect when used in combination than the additive effects of any of the individual agents when used alone. The term "greater effect" encompasses not only a reduction in symptoms of the disorder to be treated, but also an improved side effect profile, improved tolerability, improved patient compliance, improved efficacy, or any other improved clinical outcome.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, an antibody fragment, a vitamin or vitamin derivative, a carbohydrate, a toxin, a chemotherapeutic compound, or a vaccine. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. One of skill in the art can readily recognize that there is no limit as to the structural nature of the agents of the present invention.

In some embodiments, "the subject" is an animal. In some embodiments, the subject is a human being.

The term "pharmaceutically acceptable salt" refers to salts derived from a variety of organic and inorganic counter ions well known in the art. Pharmaceutically acceptable salts that will be suitable for guanabenz and guanabenz derivatives include, but are not limited to, hydrochloric acid, hydrobromic acid, sulfuric acid, nitric acid, phosphoric acid, and acetic acid.

The term "pharmaceutically acceptable carrier" refers to a solid or liquid filler, diluents, or encapsulating substance, and may include any and all solvents, media, coatings and the like. The use of such media and agents for pharmaceutically active substances is well known in the art. Other active ingredients may also be incorporated into the compositions.

The term "brain cell" may refer to any cell type found in the brain. Examples of brain cells include but are not necessarily limited to neuronal cells, neurons, glial cells, cells of the oligodendrocyte lineage, astrocytes, microglia, endothelial cells. Characteristics of these cell types are well known to those skilled in the art.

The term "a neuronal cell" refers to a cell of neuronal lineage. Exemplary cells include but are not limited to neurons, neural precursors, glial cells, cells of the oligodendrocyte lineage, astrocytes.

An "alkyl" group refers to a saturated aliphatic hydrocarbon group. The alkyl moiety, whether saturated or unsaturated, may be branched, straight chain, or cyclic. An "alkyl" moiety may, for example, have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 5 carbon atoms. The alkyl group of the compounds described herein may be designated as "C1-C4 alkyl", "C5-C8 alkyl" or similar designations. By way of example only, "C1-C4 alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Common alkyl groups include, but are in no way limited to, methyl, ethyl, propyl, isopropyl, butyl, isobutyl, tertiary butyl, pentyl, hexyl, cyclopropyl, cyclobutyl, cyclopentyl, cyclohexyl, and the like.

The term "alkoxy" as used herein means an —O-alkyl group, wherein alkyl is as defined above. Alkoxy groups include moieties such as, but not limited to, methoxy, ethoxy, n-propyloxy, i-propyloxy, n-butyloxy, i-butyloxy, t-butyloxy, pentyloxy, hexyloxy, including their isomers.

The term "aryl" as used herein refers to an aromatic carbocyclic system of about 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthol and fluorenyl.

The term "aryloxy" as used herein denotes a O-aryl group, wherein aryl is as defined above. An aryloxy group can be unsubstituted or substituted with one or two suitable substituents.

The term "halogen" or "halo" as used herein denotes fluorine, chlorine, bromine, or iodine.

The term "haloalkyl" as used herein denotes a unbranched or branched chain alkyl group as defined above wherein 1, 2, 3 or more hydrogen atoms are substituted by a halogen. Examples include, but are not limited to, 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

Subjects in Need of Treatment

In one aspect of the present invention, the treatment is administered to a subject suffering from a demyelinating disorder. In some cases, a subject suffering from a demyelinating disorder can be a subject diagnosed, suspected of having, experiencing or having experienced one or more symptom(s) of a demyelinating disorder. The symptom(s) of a demyelinating disorder include but are not limited to fatigue, somatosensory dysfunction, tingling, pain, numbness, balance problems, problems with walking, changes in vision, depression, emotional changes, mood swings, impaired cognition, muscle dysfunction, impaired muscle coordination, sexual impairment, speech impairment, swallowing impairment, bladder dysfunction, bowel dysfunction. One of ordinary skill in the art will understand that the symptom(s) of demyelinating disorders may vary widely from subject to subject, in terms of symptom manifestation, onset, and severity. In some cases, the symptom(s) may last for 24 hours and then subside. In some cases after a subject's symptom(s) have subsided, the subject may experience any of the symptom(s) at a later time (relapsing/remitting disorder). In some cases the symptom(s) may progressively worsen over time (progressive disorder).

In some cases, a subject may be diagnosed with or suspected of having a demyelinating disorder based on any combination of a number of tests and assays described below. One of ordinary skill in the art will understand that the tests and assays described below may also be used to monitor the progression of the disorder or to monitor symptom severity or symptom relapse. The term "diagnosis" as used herein encompasses the monitoring of the disorder and/or its symptom severity or relapse.

In some cases, diagnosis of the demyelinating disorder can be based on a physical exam, neurological exam, medical history, electrophysiological test, lab assay, or imaging. In some cases, a physical exam or medical history will include an assessment or history of symptoms. In some cases, the neurological exam will include an assessment of the patient's vision, reflexes, balance, coordination, and/or muscle strength.

In some cases, the electrophysiological test can involve examining the electrical impulses traveling through the nerves to determine if the impulses are moving normally or too slowly. In some cases, the electrophysiological test can involve placing wires on the scalp to test the subject's evoked potential response to certain types of stimulation. In some cases, the stimulation may be visual in nature. In other cases, the stimulation may be auditory in nature. In yet other cases, the stimulation may be somatosensory in nature. In still yet other cases, the stimulation may involve stimulation of muscle responses in the leg(s) or arm(s). One of ordinary skill in the art will understand that the measurement of normal speed evoked potentials in a subject does not necessarily preclude a diagnosis of a demyelinating disorder.

In some cases, the lab assay may include a cerebrospinal fluid (CSF) assessment of biomarkers associated with a demyelinating disorder. In some cases, CSF assessment may involve an assessment of immunoglobulin levels in the cerebrospinal fluid. It is known in the art that an increase in immunoglobulin concentrations in CSF is associated with demyelinating disorders. In some embodiments, the assessment of immunoglobulin may involve taking an IgG index (a comparison between IgG levels in the CSF and in blood serum). In some cases, an elevated IgG index can be used to support diagnosis of a demyelinating disorder. In some embodiments, assessment of CSF may involve separation of CSF proteins by electrophoresis and identification of oligoclonal immunoglobulin bands by electrophoresis. In some cases, oligoclonal bands from CSF appear as strips on the electrophoresis gel, and may be visualized by Coomassie Blue staining or other staining technique. In some cases, the presence of oligoclonal immunoglobulin in CSF may be used to support diagnosis of a demyelinating disorder. In some embodiments, assessment of CSF may involve determination of overall protein levels in the CSF sample. In some cases, elevated protein levels in the CSF may be used to support diagnosis of a demyelinating disorder. In some cases, elevated CSF protein levels may be used to support diagnosis of relapse of a demyelinating disorder. In some embodiments, assessment of CSF may involve measuring a cell count of the CSF sample. In some embodiments, a higher cell count in the CSF sample can be used to support diagnosis of a demyelinating disorder. In some cases, the cells found in CSF may be T-lymphocytes. In some cases, the presence of T-lymphocytes in CSF may be used to support diagnosis of a demyelinating disorder.

In some embodiments, the lab assay may involve testing for the presence of autoantibodies in a biological sample from the subject. In some embodiments, the sample is a blood serum sample. In some embodiments, the autoantibodies to be assayed are directed to myelin or a myelin-associated protein. In some embodiments, the autoantibody to be assayed is a myelin basic protein antibody. In some embodiments, the autoantibody to be assayed is a myelin oligodendrocyte glycoprotein antibody. In some embodiments, the assay to detect autoantibodies is a western blot assay.

In some cases, imaging can involve magnetic resonance imaging (MRI) of myelin in the central nervous system of a subject, comprising the subject's brain and spinal cord. In some cases, magnetic resonance imaging can involve intravenous injection of gadolinium-based tracers to visualize the white matter. In some cases, magnetic resonance imaging can be used to identify white matter plaques and/or lesions associated with the disease. In some cases, white matter plaques and/or lesions exhibit high intensity on T2-weighted and FLAIR images and low intensity on T1-weighted scans. One of ordinary skill in the art will realize that intensities of white matter plaques and/or lesions will vary depending on magnetic field strength, pulse sequence parameters, and partial volume effects. In some cases, the white mater plaques and/or lesions may show partial or complete destruction of myelin (demyelination). In some cases, white matter plaques and/or lesions may occur in the brain. In some cases, white matter plaques and/or lesions may occur in the spinal cord. In some cases, the diagnosis is based on the presence of two or more white matter plaques and/or lesions. In some cases, the demyelination may occur in a perivenular distribution. In some cases, the demyelination may be associated with gliosis. In some cases, the demyelination may be associated with hallmarks of inflammation. In some cases, the hallmarks of inflammation may include infiltration of mononuclear cells and/or lymphocytes. One of ordinary skill in the art will understand that the lack of white matter plaques and/or lesions visualized by imaging does not necessarily preclude a diagnosis of a demyelinating disorder, as some lesions may be too small to be visualized by imaging.

In some cases, the symptom(s) of a demyelinating disorder may overlap with a number of other diseases or syndromes. In some cases, diagnosis of a demyelinating disorder may involve ruling out other possible conditions that may cause similar symptom(s). In some cases, conditions that may be ruled out to support a diagnosis of a demyelinating disorder include, but are not limited to, stroke, alcoholism, emotional disorders, Lyme disease, chronic fatigue syndrome, fibromyalgia, AIDS, cervical spondylosis, hyperthyroidism, scleroderma, Sjogren's syndrome, systematic lupus erythematosus. Methods for ruling out the above disorders are known to those skilled in the art.

In another aspect of the present invention, the treatment is administered to a subject at increased risk for developing a demyelinating disorder. A number of environmental and genetic factors have been found to be associated with increased risk for demyelinating disorders. In some embodiments of the invention, a subject may be considered to have an increased risk for developing a demyelinating disorder based on any combination of the risk factors described herein. One of ordinary skill in the art will understand that a greater number of risk factors that can be applied to a subject may correlate with greater risk of the subject developing a demyelinating disease, however, a subject may be considered to be at increased risk for developing a demyelinating disorder based on even one of the risk factors described herein.

In some embodiments, the subject may be considered to be at increased risk for developing a demyelinating disorder if the subject is experiencing or has experienced a clinically isolated syndrome, wherein the clinically isolated syndrome is a first or isolated neurologic episode that lasts at least 24 hours, wherein the subject experiences at least one or more symptom(s) described herein. The clinically isolated syndrome may be monofocal, wherein the subject experiences a single neurologic symptom described herein. The clinically isolated syndrome may be multifocal, wherein the subject experiences more than one symptom described herein. In some cases, the clinically isolated syndrome may be associated with inflammation and/or demyelination in one or more sites in the central nervous system.

In some embodiments, the subject may be considered to be at increased risk for developing a demyelinating disorder if the subject exhibits one or more MRI white matter plaques and/or lesions without any discernable clinical symptoms. Methods for assessing white matter plaques and/or lesions are described herein.

In some embodiments, the subject may be considered to be at increased risk for developing a demyelinating disorder if the subject exhibits CSF biomarkers associated with a demyelinating disorder. CSF biomarkers associated with a demyelinating disorder have been described herein.

In some embodiments, a subject may be considered to be at increased risk for developing a demyelinating disorder if the subject has a family history of a demyelinating disorder. In some embodiments, a family history of a demyelinating disorder may involve any relative of the subject being diagnosed or suspected of having a demyelinating disorder. In some embodiments, a family history of a demyelinating disorder may include an immediate family member having been diagnosed or suspected of having a demyelinating disorder. In some cases, the family member diagnosed or suspected of having a demyelinating disorder may be a parent. In some cases, the family member may be a sibling. In some cases, the sibling may be an identical twin. In some cases, the family member may be a son or daughter. In some cases, the relative of the subject can be outside the immediate family, e.g., a first cousin, a second cousin, a third cousin, an aunt, an uncle, a second or third aunt, a second or third uncle, a niece, a nephew, a second or third niece, a second or third nephew.

In some embodiments, a subject may be considered to be at increased risk for developing a demyelinating disorder if the subject harbors a particular allele, polymorphism, or haplotype associated with a demyelinating disorder. Methods for determining whether a subject harbors an allele, polymorphism, or haplotype are known to those of ordinary skill in the art, and may include but are not limited to genotyping methods, exome or genome sequencing methods, or haplotype analysis. In some embodiments, the allele, polymorphism, or haplotype involves the Major Histocompatibility Complex class 2 (MHC II), otherwise known as human leukocyte antigen (HLA). In some cases, the allele is the HLA-DR2 allele, which has previously been associated with multiple sclerosis. In some cases, the allele is the DRB1*1501 allele. In some cases, the allele is the DQA1*0102 allele. In some cases, the allele is the DQB1*0602 allele. In some cases, the haplotype is the HLA class II DR15 haplotype (DRB1*1501-DQA1*0102-DQB1*0602). In some embodiments, the polymorphism may be a single nucleotide polymorphism (SNP) in a gene encoding an interleukin receptor. In some embodiments, the interleukin receptor may be interleukin 2 receptor-alpha (IL2R-alpha). In some embodiments, the IL2R-alpha SNP may be rs12722489. In some embodiments, the IL2R-alpha SNP may be rs2104286. In some embodiments, the interleukin receptor may be interleukin 7 receptor-alpha (IL7R-alpha). In some embodiments, the IL7R-alpha SNP may be Rs6897932. In some embodiments, the IL7R-alpha SNP may cause a reduction in the amount of IL7R-alpha protein present at the surface of T-cells. One of ordinary skill in the art will understand that the above list may not be a complete list of genetic risk factors for demyelinating disorders.

In some embodiments, the subject may be considered to be at increased risk for developing a demyelinating disorder if the subject or a relative of the subject suffers or has suffered from another autoimmune disorder. In some cases, the subject or relative may suffer or have suffered from irritable bowel syndrome. In some cases, the subject or relative may suffer or have suffered from autoimmune thyroid disease. In some cases, the subject or relative may suffer or have suffered from rheumatoid arthritis. In some cases, the subject or relative may suffer or have suffered from Crohn's Disease. In some cases, the subject or relative may suffer or have suffered from Type 1 Diabetes.

In some embodiments, the subject may be considered to be at increased risk for developing a demyelinating disorder if the subject has experienced a disruption of the blood-brain barrier. Possible causes of blood-brain barrier disruption include but are not limited to, traumatic brain injury, viral infection, HIV infection, inflammation of the meninges, stroke, among others. In some embodiments, blood brain barrier disruption may be indicated by the detection of serum markers in CSF. In some embodiments, the serum markers may include: serum S-100beta. In some embodiments, blood-brain barrier disruption may be indicated by the presence of one or more white matter plaques and/or lesions as visualized by MRI. Methods for visualizing white matter plaques and/or lesions are described herein.

In some embodiments, a subject may be considered to be at increased risk for developing a demyelinating disorder if the subject is female.

In some embodiments, a subject may be considered to be at increased risk for developing a demyelinating disorder if the subject is between 15 and 60 years of age, or between 20 and 50 years of age, or around the age of 20-30.

In some embodiments, a subject may be considered to be at increased risk for developing a demyelinating disorder if the subject is of Caucasian descent. In some embodiments, a subject may be considered to be at increased risk for developing a demyelinating disorder if the subject is of northern European descent. In some embodiments, a subject may be considered to be at increased risk for developing a demyelinating disorder if the subject is of Scottish descent.

In some embodiments, a subject may be considered to be at increased risk for developing a demyelinating disorder if the subject has experienced a viral infection. In some embodiments, the viral infection may be from a human herpesvirus. In some embodiments, the human herpesvirus may be Epstein-Barr virus. In some embodiments, the human herpesvirus may be human herpesvirus 6 (HHV-6).

In some embodiments, the subject may be considered to be at increased risk for a demyelinating disease if the subject has had insufficient exposure to sunlight.

In some embodiments, the subject may be considered to be at increased risk for a demyelinating disease if the subject has a Vitamin D deficiency. In some cases, the subject may be absorbing or ingesting less than 1000 U of Vitamin D per day.

In some embodiments, the subject may be considered to be at increased risk for a demyelinating disease if the subject has ever been exposed to cigarette smoke.

Uses of Guanabenz or Guanabenz Derivatives

The present invention provides the use of a compound of Formula I (below):

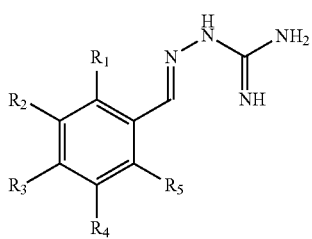

Formula I or derivative thereof, or a pharmaceutically acceptable salt thereof, wherein $R_1$, $R_2$, $R_3$, $R_4$, and $R_5$ are independently hydrogen, deuterium, halogen, haloalkyl, alkyl, alkoxy, hydroxyl, aryl, or aryloxy, for the treatment of a variety of demyelinating disorders. In a preferred embodiment, the compound may be a compound of Formula II (below):

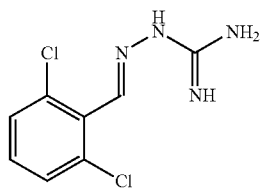

Formula II herein referred to as "guanabenz" or a pharmaceutically acceptable salt thereof.

In some aspects of the present invention, a compound of Formula I or Formula II may be used to increase viability of a neuronal cell or cell of the oligodendrocyte lineage in a subject suffering from a demyelinating disorder. One of skill in the art may use various assays, tests, diagnostic methods, or indicators to determine whether administration of a compound of Formula I or Formula II increases the viability of a neuronal cell. In some embodiments, one may determine if a compound of Formula I or Formula II has improved viability of a neuronal cell based on a cell culture assay. Examples of useful cell culture assays include but are not limited to counting the number of cells in a cell population that has been contacted with a compound of Formula I or Formula II for comparison to the number of cells in a cell population that has not been contacted with guanabenz, measuring viability by a LIVE/DEAD® assay (Invitrogen), measuring cell death or apoptosis by a TUNEL assay. In some embodiments, one may determine if a compound of Formula I or Formula II has improved viability of a neuronal cell based on an ex vivo assay. Examples of ex vivo assays include but are not limited to, staining ex vivo tissue samples with cresyl violet and counting the number of stained cells, staining ex vivo tissue samples using a TUNEL assay, staining ex vivo tissue samples with markers of brain cells or neuronal cells and counting the number of cells containing the marker. Examples of useful markers include but are not limited to, NeuN (a neuron-specific marker), GFAP (an astrocyte-specific marker), oligodendrocyte lineage specific markers such as oligodendrocyte specific protein, oligodendrocyte marker O1, oligodendrocyte marker O4, etc. In some embodiments, one may determine if a compound of Formula I or Formula II has improved viability of a neuronal cell based on non invasive, in vivo assays. In some embodiments, in vivo imaging of neurodegeneration may be used to indicate viability, wherein reduction of neurodegeneration is indicative of increased viability. In some embodiments, neurodegeneration in vivo may be indicated by reduction in white or gray matter volume as determined by MRI, reduction in the number or integrity of axons as visualized by diffusion tensor imaging, or by the appearance of plaques or lesions in the brain. In some embodiments, methods for the non-invasive, in vivo assessment of apoptosis may be used to determine viability, wherein reduction of apoptosis is indicative of increased viability. Methods for the non-invasive, in vivo assessment of apoptosis are in development, for example, a radiolabeled analog is currently being evaluated as a PET probe in a phase II study (Adv. Drug Deliv Rev 2005; 57: 1087-1108, herein incorporated by reference). In some embodiments, increased viability of neuronal cells or cells of the oligodendrocyte lineage may also result in symptomatic improvement, e.g., improvement or delayed onset of any of the symptom(s) listed herein.

In some embodiments, administration of a compound of Formula I or Formula II may result in an increase in viability of about 0.1%, 0.5%, 1%, 5%, 10%, 15%, 20%, 30%, 40%, 50%, 60%, 70%, 80%, 90%, 100%, or more than 100%. In some embodiments, a compound of Formula I or Formula II may increase viability by a range of about 0.1%-10%, about 0.5%-20%, about 1%-30%, about 5%-40%, about 10%-60%, about 20%-80%, about 30%-90%, about 40% to more than 100%.

Protecting Brain Cells from Inflammation

In some aspects of the present invention, a compound of Formula I or Formula II may be used to protect brain cells from inflammation. One of skill in the art may use various assays, tests, diagnostic methods, or indicators to determine whether a subject is in need of a compound of Formula I or Formula II for the protection of brain cells from inflammation, or to determine if a cell of the oligodendrocyte lineage of a subject has likely been exposed to an inflammatory agent. In some cases, a subject may be determined to be in need of protection from inflammation or exposed to an inflammatory agent based on CSF assays described herein, or by PET imaging of [$^{11}$C](R)-PK11195, which binds to activated microglia. In some cases, subjects that harbor one or more haplotypes or genetic variants associated with demyelinating diseases may be considered to likely harbor neuroinflammation, and thus may be considered subjects in need of a compound of Formula I or Formula II for the protection of brain cells against inflammation. In some cases, a subject may be deemed likely to have been exposed to an inflammatory agent if the subject is diagnosed as suffering from a demyelinating disorder or deemed to be at increased risk for a demyelinating disorder based on diagnostic assays and criteria described herein.

In some embodiments, one of skill in the art may use various assays, tests, diagnostic methods, or indicators of inflammation to determine whether the compositions and methods of the present invention provide protection of brain cells from inflammation. In some cases, indications of protection of cells from inflammation may comprise: reduction of the number or size of white matter plaques and/or lesions, improved axonal integrity, which may be visualized through diffusion tensor imaging, reduced markers of apoptosis. In some cases, protection of cells from inflammation may comprise: reduced demyelination, reduced progressive increase in the number or size of white matter plaques and/or lesions, or improved remyelination. Protection of brain cells from inflammation may also result in symptomatic improvement, e.g., improvement or delayed onset of any of the symptom(s) listed herein. In some embodiments, in vitro assays may be used to determine whether the compound(s) of the present invention provide protection of brain cells from inflammation, for example, by administering the compound(s) to a cultured brain cell or population of cultured brain cells that have been contacted with an inflammatory agent (e.g., interferon-γ, reactive oxygen species, inflammatory cytokines), and determining viability of the cell or population of cells.

In some embodiments of the present invention, the compound(s) of the present invention may reduce indicators of inflammation as described herein by about 1%, about 2%, about 3%, about 4%, about 5%, about 10%, about 15%, about 20%, about 25%, about 30%, about 40%, about 50%, about 60%, about 70%, about 80%, about 90%, or about 100%. In some embodiments, the compound(s) may reduce indicators of inflammation by a range of about 1-10%, about 2-20%, about 5-30%, about 10-40%, about 20-100%.

Treating a Symptom(s)

In some embodiments of the present invention, the compound(s) described herein may be used to treat a symptom of a demyelinating disorder. Exemplary symptoms of demyelinating disorders are described herein. Methods of diagnosing or monitoring symptoms of demyelinating disorders are described herein.

In some embodiments, administration of the compound(s) of the present invention may result in reducing the severity of symptoms by about 1%, about 2%, about 3%, about 4%, about 5%, about 10%, about 15%, about 20%, about 25%, about 30%, about 40%, about 50%, about 60%, about 70%, about 80%, about 90%, or about 100%. In some embodiments, the compound(s) may reduce the severity of symptom(s) by a range of about 1-10%, about 2-20%, about 5-30%, about 10-40%, about 20-100%. In yet other embodiments, the compound(s) may reduce the severity of symptom(s) by at least 25%.

Delaying Onset of Symptom(s)

In some aspects, the compositions and methods of the present invention may be used to delay onset of symptom(s) of a demyelinating disorder. Subjects that may be a good candidate for this indication may include: subjects that have presented with one or more clinically silent lesions as described herein, but who has not yet experienced symptom(s) of a demyelinating disorder, subjects who have experienced a single isolated episode but who has not yet been diagnosed with a demyelinating disorder, subjects who are at increased risk for developing a demyelinating disorder, or subjects that are in a remission phase of the disorder. In some embodiments, the subject in a remission phase of a demyelinating disorder may have experienced a reduction in symptom(s) severity for at least one or at least two days, without experiencing any worsening of any symptoms of the disorder.

In some embodiments, delayed onset of symptoms may be indicated by monitoring the symptoms of the subject on a regular basis, e.g., by completing a symptom checklist about once a day. In some embodiments, delayed onset of symptoms may be indicated by physician assessment using any of the diagnostic methods described herein. In some embodiments, delayed onset of symptoms may be indicated by comparing the frequency of symptom onset of the subject before and after the start of guanabenz administration, or by comparing the frequency of symptom onset of a population of subjects administered guanabenz to frequency of symptom onset of a population of subjects not exposed to guanabenz and/or optionally any other agent useful in the treatment of a demyelinating disorder.

In some embodiments, the methods and compositions of the present invention may result in a delay of symptom onset of at least about 1 day, at least about 2 days, at least about 3 days, at least about 4 days, at least about 5 days, at least about 6 days, at least about 1 week, at least about 2 weeks, at least about 1 month, at least about 2 months, at least about 4 months, at least about 6 months, at least about 1 year, at least about 2 or more years.

Reducing Relapse

In some aspects, the compositions and methods of the present invention may be used to prevent or reduce severity of relapse of a demyelinating disorder. Methods for treatment regimens for reducing relapse of, and methods for monitoring relapse of a demyelinating disorder, are described herein.

In some embodiments, administration of the compound(s) described herein may result in a reduction of relapse incidents by about 1%, about 2%, about 4%, about 6%, about 8%, about 10%, about 20%, about 30%, about 40%, about 50%, about 60%, about 70%, about 80%, about 90%, or about 100%. In some embodiments, administration of the compound(s) may reduce the frequency of relapse to an average of about 1 episode a week, about 1 episode every two weeks, about 1 episode a month, about 1 episode every 2 months, about 1 episode every 4 months, about 1 episode every 6 months, about 1 episode a year, or about less than an episode a year.

In some embodiments, the compositions and methods of the present invention may result in a reduction of severity of relapse. Severity of relapse may be indicated by monitoring the severity of symptom(s) during relapse. In some embodiments, administration of compound(s) described herein may result in a reduction of relapse severity by about 1%, about 2%, about 4%, about 6%, about 8%, about 10%, about 20%, about 30%, about 40%, about 50%, about 60%, about 70%, about 80%, about 90%, about 100%. In some embodiments, the compound(s) may reduce the severity of relapse by a range of about 1-10%, about 2-20%, about 5-30%, about 10-40%, about 20-100%. In yet other embodiments, the compound(s) may reduce the severity of relapse by at least 25%. In still yet other embodiments, the compound(s) may reduce the severity of relapse by at least 50%.

Exemplary Compounds

The subject method utilizes a compound of Formula I:

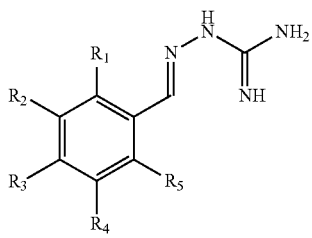

Formula I or a derivative thereof, or a pharmaceutically acceptable salt thereof, wherein: $R_1$, $R_2$, $R_3$, $R_4$, and $R_5$ are independently hydrogen, deuterium, halogen, haloalkyl, alkyl, alkoxy, hydroxyl, aryl, or aryloxy. Exemplary compounds include guanabenz and guanabenz derivatives. In some embodiments, the R1 and R5 groups are not hydrogen. In some embodiments, the R1 and R5 groups are halogen. In some embodiments, the compound is of Formula II:

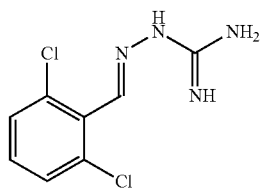

Formula II

In some embodiments, the compound of Formula I or its derivatives may be synthesized using methods known to those skilled in the art (see, e.g., U.S. Pat. No. 3,975,533 or 7,932,422, herein incorporated by reference). In other embodiments, the compound of Formula II (Guanabenz, CAS No. 5051-62-7) may be synthesized using methods known to those skilled in the art (see, e.g., U.S. Pat. No. 3,982,020, Bioconjugate Chem. 21:279-288, 2010, herein incorporated by reference).

Pharmaceutical Compositions

In general, the guanabenz compounds and compositions can be formulated as pharmaceutically acceptable free base or salt forms. Pharmaceutically acceptable salts are described herein. In preferred embodiments, the pharmaceutically acceptable salt compositions of Formula I or Formula II are acetate salt compositions. In other embodiments, the pharmaceutically acceptable salt compositions of Formula I or Formula II are chlorine salt compositions.

In some embodiments, the compositions comprising an effective amount of a compound of Formula I or Formula II may include a pharmaceutically acceptable carrier. In some embodiments, a pharmaceutically acceptable carrier for the present compositions may include, but are not limited to, amino acids, peptides, biological polymers, non-biological polymers, simple sugars or starches, inorganic salts, and gums, which may be present singly or in combinations thereof. In some embodiments, the peptides used in the acceptable carrier may be gelatin. In some embodiments, the peptides used in the acceptable carrier may be albumin. In some embodiments, cellulose or its derivatives may be used in the pharmaceutically acceptable carrier. In some embodiments, the sugar used in the acceptable carrier may be lactose. In some embodiments, the sugar used in the acceptable carrier may be glucose. In other embodiments, useful sugars may include but are not limited to, fructose, galactose, lactitol, maltitol, maltose, mannitol, melezitose, myo-inositol, palatinate, raffinose, stachyose, sucrose, trehalose, xylitol, hydrates thereof, and combinations of thereof. In some embodiments, binders may be included in the pharmaceutically acceptable carrier. Examples of binders include, but are not limited to, starches (for example, corn starch or potato starch), gelatin; natural or synthetic gums such as acacia, sodium alginate, powdered tragacanth, guar gum, cellulose or cellulose derivatives (for example, methylcellulose, ethyl cellulose, cellulose acetate); microcrystalline cellulose, polyvinyl pyrrolidone, and mixtures thereof. In some embodiments, the inorganic salts used in the acceptable carrier may be a magnesium salt, for example, magnesium chloride or magnesium sulfate. In some embodiments, other inorganic salts may be used, for example, calcium salts. Examples of calcium salts include, but are not limited to, calcium chloride, calcium sulfate. Other examples of substances which may be used in the pharmaceutically acceptable carrier may include, but are not limited to, vegetable oils, such as peanut oil, cottonseed oil, olive oil, corn oil; polyols such as glycerin, propylene glycol, polyethylene glycol; pyrogen-free water, isotonic saline, phosphate buffer solutions; emulsifiers, such as the Tweens®); wetting agents, lubricants, coloring agents, flavoring agents, preservatives.

The term "wetting agents" may be used interchangeably with "surfactants", and refers to substances that lower the surface tension of a liquid, thus allowing the liquid to spread more easily. Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. A useful parameter that may be used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are generally considered to be compounds having an HLB value equal to or less than about 10. However, HLB value of a surfactant merely provides a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts, fatty acid derivatives of amino acids, glyceride derivatives of amino acids, fusidic acid salts, oligopeptides, and polypeptides, oligopeptides, and polypeptides, lecithins and hydrogenated lecithins, lysolecithins and hydrogenated lysolecithins, phospholipids and derivatives thereof, fatty acid salts, lysophospholipids and derivatives thereof, carnitine fatty acid ester salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Within the aforementioned group, ionic surfactants include, but are not limited to, lecithins, lysolecithin, phospholipids, lysophospholipids and derivatives thereof, carnitine fatty acid ester salts, fatty acid salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Ionic surfactants may be the ionized forms of lactylic esters of fatty acids, lecithin, lysolecithin, phosphatidylethanolamine, phosphatidylcholine, phosphatidylglycerol, phosphatidic acid, phosphatidylserine, lysophosphatidylcholine, lysophosphatidylserine, lysophosphatidylethanolamine, lysophosphatidylglycerol, lysophosphatidic acid, PEG-phosphatidylethanolamine, PVP-phosphatidylethanolamine, stearoyl-2-lactylate, stearoyl lactylate, succinylated mono-glycerides, mono/diacetylated tartaric acid esters of mono/diglycerides, citric acid esters of mono/diglycerides, cholylsarcosine, caproate, caprylate, caprate, laurate, myristate, palmitate, oleate, linoleate, linolenate, stearate, ricinoleate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides, alkylthioglucosides, alkylmaltosides, lauryl macrogolglycerides, polyoxyalkylene alkyl ethers such as polyethylene glycol alkyl ethers, polyoxyalkylene alkylphenols such as polyethylene glycol alkyl phenols, polyethylene glycol glycerol fatty acid esters, polyoxyalkylene alkyl phenol fatty acid esters such as polyethylene glycol fatty acids monoesters and polyethylene glycol fatty acids diesters, polyglycerol fatty acid esters, polyoxyethylene-polyoxypropylene block copolymers and mixtures thereof, polyoxyalkylene sorbitan fatty acid esters such as polyethylene glycol sorbitan fatty acid esters, hydrophilic transesterification products of a polyol with at least one member of the group consisting of glycerides, vegetable oils, hydrogenated vegetable oils, fatty acids, and sterols, polyoxyethylene sterols and derivatives or analogues thereof, polyoxyethylated vitamins and derivatives thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-12 oleate, PEG-15 oleate, PEG-20 oleate, PEG-20 laurate, PEG-32 dilaurate, PEG-32 laurate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-20 trioleate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-50 hydrogenated castor oil, PEG-40 castor oil, PEG-35 castor oil, PEG-60 castor oil, PEG-40 palm kernel oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, but are not limited to, fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar ethers, sugar esters, hydrophobic transesterification products of a polyol with at least one member of the group consisting of glycerides, vegetable oils, hydrogenated vegetable oils, fatty acids and sterols, oil-soluble vitamins/vitamin derivatives, lactic acid derivatives of mono- and di-glycerides, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In some embodiments, lubricants that may be used in the pharmaceutical composition include, but are not limited to, agar, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, or mixtures thereof. Additional lubricants include, by way of example, a syloid silica gel, a coagulated aerosol of synthetic silica, or mixtures thereof. A lubricant can optionally be added, in an amount of less than about 1 weight percent of the pharmaceutical composition.

In some embodiments, the composition may include a solubilizer to ensure good solubilization of the compound and to reduce precipitation of the compound of the present invention. A solubilizer may be used to increase solubility of the compound or other active ingredients, or may be used to maintain the composition as a homogeneous solution or dispersion. Examples of suitable solubilizers include but are not limited to, alcohols and polyols such as ethanol, isopopropanol, polyvinyl alcohol, gelatin, mannitol, sodium carboxymethyl cellulose (CMCNa), povidone, propylene glycol, polyethylene glycol, polyvinyl pyrolidone, glycerin, cyclodextrins or cyclodextrin derivatives, polyethylene glycol ethers of molecular weight averaging about 200 to about 6000, such as PEG, amides and other nitrogen-containing compounds such as 2-pyrrolidone, 2-piperidone, epsilon.-caprolactam, N-alkylpyrrolidone, N-hydroxyalkylpyrrolidone, N-alkylpiperidone, N-alkylcaprolactam, dimethylacetamide and polyvinylpyrrolidone, esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, water, or mixtures and/or combinations thereof.

Mixtures of solubilizers may also be used. Examples include, but not limited to, ethyl oleate, ethyl caprylate, triacetin, triethylcitrate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, transcutol, propylene glycol, glycofurol and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example, to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 75%, 100%, or up to about 200% by weight, based on the combined weight of the drug, and other excipients. If desired, very small amounts of solubilizer may also be used, such as 5%, 2%, 1%, 0.5% or even less. Typically, the solubilizer may be present in an amount of about 1% to about 100%, more typically about 5% to about 25% by weight.

In some embodiments, the composition may include one or more pharmaceutically acceptable additives, which may include, but are not limited to, detackifiers, anti-foaming agents, buffering agents, antioxidants, polymers, preservatives, chelating agents, odorants, opacifiers, suspending agents, fillers, plasticizers, and mixtures thereof.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound of Formula I or Formula II in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the concentration of the compound of Formula I or Formula II is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% of the pharmaceutical composition by w/w, w/v or v/v. v/v.

In some embodiments, the concentration of the compound of Formula I or Formula II is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v. v/v.

In some embodiments, the amount of the compound of Formula I or Formula II in the pharmaceutical composition is about 0.00001 mg, 0.0001 mg, 0.001 mg, 0.005 mg, 0.01 mg, 0.05 mg, 0.1 mg, 0.25 mg, 0.5 mg, 1 mg, 2 mg, 4 mg, about 8 mg, about 16 mg, about 32 mg, about 64 mg, about 100 mg, about 200 mg, about 500 mg, about 1 g, about 2 g, about 5 g, about 10 g.

In some embodiments, the pharmaceutical compositions of Formula I or Formula II may be manufactured by Ivax Pharmaceuticals. In some embodiments, the pharmaceutical compositions of Formula I or Formula II may be manufactured by Teva Pharmaceuticals. In some embodiments, the pharmaceutical compositions of Formula I or Formula II may be manufactured by Sandoz Inc. In some embodiments, the pharmaceutical compositions of Formula I or Formula II may be manufactured by Watson Laboratories Inc. In some embodiments, the pharmaceutical compositions of Formula I or Formula II may be manufactured by Wyeth Ayerst Laboratories.

In some cases, the pharmaceutical compositions of Formula I or Formula II may be packaged by Ivax Pharmaceuticals. In some cases, the pharmaceutical compositions of Formula I or Formula II may be packaged by Letco Medical Inc. In some cases, the pharmaceutical compositions of Formula I or Formula II may be packaged by Murfreesboro Pharmaceuticals. In some cases, pharmaceutical compositions of Formula I or Formula II may be packaged by the Pharmaceutical Utilization Management Program VA., Inc.

In some cases, the pharmaceutical compositions of Formula I or Formula II may comprise an additional agent. The additional agent may be an agent useful in the treatment of a demyelinating disorder. Examples of other agents useful in the treatment of demyelinating disorders include, but are not limited to, interferon β, IFN β-1a (brand names: AVONEX, REBIF), IFNβ-1b (brand name: BETASERON), glatiramer acetate (COPAXONE, Copolymer-1), natalizumab (TYSABRI), mitoxantrone ($C_{22}H_{28}N_4O_6$.2HCl), methylprednisone, methylprednisolone, thalidomide, fingolimod (GILENIA), dimethyl fumarate (BG-12), teriflunomide (AUBAGIO), anti-LINGO antibody, alemtuzumab (CAMPATH), dalfampridine, PEG-interferon beta-1a (BIIB017), daclizumab (ZENAPAX), laquinimod, and ocrelizumab. Accordingly, a pharmaceutical composition of Formula I or Formula II may comprise one or more agents selected from the group consisting of interferon β, IFN β-1a (brand names: AVONEX, REBIF), IFNβ-1b (brand name: BETASERON), glatiramer acetate (COPAXONE, Copolymer-1), natalizumab (TYSABRI), mitoxantrone ($C_{22}H_{28}N_4O_6 \cdot 2HCl$), methylprednisone, methylprednisolone, thalidomide, fingolimod (GILENIA), dimethyl fumarate (BG-12), teriflunomide (AUBAGIO), anti-LINGO antibody, alemtuzumab (CAMPATH), dalfampridine, PEG-interferon beta-1a (BIIB017), daclizumab (ZENAPAX), laquinimod, and ocrelizumab.

Described below are some non-limiting examples of pharmaceutical compositions.

Pharmaceutical Compositions for Oral Administration

In some embodiments, the invention provides a pharmaceutical composition comprising an effective amount of a compound of Formula I or Formula II for oral administration containing at least one therapeutic agent and a pharmaceutically acceptable carrier for oral administration. In some embodiments, pharmaceutically acceptable carriers described herein can be suitable for oral administration.

In some embodiments, the pharmaceutical composition comprising an effective amount of a compound of Formula I or Formula II for oral administration is a solid pharmaceutical composition. In some embodiments, the solid pharmaceutical composition may be presented as discrete oral dosage forms. Non-limiting examples of discrete oral dosage forms include tablets, capsules, caplets, gelatin capsules, sustained release formulations, lozenges, thin films, lollipops, chewing gum.

In some embodiments, discrete oral dosage forms such as tablets may be coated by known techniques to delay or prolong absorption in the gastrointestinal tract, thus providing a sustained action of a longer period of time. In some cases, such sustained release may be beneficial to reduce side-effects, such as drowsiness. In some embodiments, the compound of Formula I or Formula II may be mixed with one or more inert solid diluents, such as calcium carbonate or calcium phosphate. In some embodiments, the compound of Formula I or Formula II may be presented as soft gelatin capsules, wherein the compound is mixed with water or an oil medium, such as peanut oil, or olive oil, for example.

In some embodiments, the pharmaceutical composition comprising an effective amount of a compound of Formula I or Formula II for oral administration is a liquid pharmaceutical composition. Non-limiting examples of liquid compositions for oral administration include hydrophilic suspensions, emulsions, liquids, gels, syrups, slurries, solutions, elixirs, softgels, tinctures, hydrogels.

In some embodiments, solid or liquid compositions comprising an effective amount of a compound of Formula I or Formula II for oral administration may also comprise various sweetening or flavoring agents, or coloring agents. Examples of coloring agents include dyes suitable for food such as those known as F.D. & C. dyes and natural coloring agents such as grape skin extract, beet red powder, beta carotene, annato, carmine, turmeric, paprika, and so forth. Derivatives, analogues, and isomers of any of the above colored compound also may be used.

Such dosage forms may be prepared by methods well known to those skilled in the art, e.g., in a pharmacy. Such methods would comprise bringing the compound of Formula I or Formula II into association with the pharmaceutically acceptable carrier.

This invention further encompasses anhydrous pharmaceutical compositions and dosage forms comprising an effective amount of a compound of Formula I or Formula II, since water may facilitate the degradation of the compounds. In some embodiments, the anhydrous pharmaceutical compositions and dosage forms of the invention may be prepared using anhydrous or low moisture containing ingredients. In some embodiments, the anhydrous pharmaceutical compositions and dosage forms of the invention may be prepared under low humidity or low moisture conditions. In some embodiments, the pharmaceutical compositions of the present invention which contain lactose may be made anhydrous if substantial contact with moisture and/or humidity during manufacturing, packaging, and/or storage is expected. In some embodiments, an anhydrous pharmaceutical composition comprising an effective amount of a compound of Formula I or Formula II may be prepared and stored such that its anhydrous nature is maintained. For example, the anhydrous compositions may be packaged using materials known to prevent exposure to water such that they can be included in suitable formulary kits, examples of which include, but are not limited to, hermetically sealed foils, plastic or the like, unit dose containers, blister packs, and strip packs.

Pharmaceutical Compositions for Injection or Parenteral Administration

In some aspects, the present invention provides pharmaceutical compositions comprising an effective amount of a compound of Formula I or Formula II for parenteral administration for the treatment of various demyelinating disorders. "Parenteral administration" refers to routes of administration other than the gastro-intestinal tract. Examples of parenteral administration include, but are not limited to, intravenous injection, subcutaneous injection, intramuscular injection, infusion, or implantation. In some embodiments, infusion may be intradermal, or subcutaneous, or through a transdermal implant. In some cases, infusion may be intracerebral, intracerebrovascular, or epidural. Pharmaceutical compositions for parenteral administration are well known in the art. Examples of the compositions for parenteral administration are disclosed in the following references which are hereby incorporated by reference: US 2006/0287221, U.S. Pat. Nos. 5,244,925, 4,309,421, 4,158,707, 5,164,405).

In some embodiments, compositions comprising an effective amount of a compound of Formula I or Formula II for parenteral administration may include aqueous solutions and/or buffers commonly used for injection and/or infusion. Commonly used aqueous buffers and/or solutions may include, but are not limited to sodium chloride solutions of about 0.9%, phosphate buffers, Lactated Ringer's solution, Acetated ringer's solution, phosphate buffered saline, citrate buffers, Tris buffers, histidine buffers, HEPES buffers, glycine buffers, N-glycylglycine buffers, and the like. Other pharmaceutically acceptable carriers for parenteral administration may include ethanol, glycerol, propylene glycol, cyclodextrin and cyclodextrin derivatives, vegetable oils, and the like.

In some embodiments, pharmaceutical compositions comprising an effective amount of a compound of Formula I or Formula II for injection and/or infusion may also contain preservatives present in amounts that effectively prevent or reduce microbial contamination or degradation. Various agents, e.g., phenol, m-cresol, benzyl alcohol, parabens, chlorobutanol, methotrexate, sorbic acid, thimerosol, ethyl hydroxybenzoate, bismuth tribromophenate, methyl hydroxybenzoate, bacitracin, propyl hydroxybenzoate, erythromycin, 5-fluorouracil, doxorubicin, mitoxantrone, rifamycin, chlorocresol, benzalkonium chlorides, may be used to prevent or reduce contamination.

In some embodiments, sterile solutions may be prepared by incorporating the compound of Formula I and/or II in the required amount in the appropriate solvent with various other ingredients as described herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain methods of preparation include but are not limited to vacuum-drying and freeze-drying techniques which yield a powder of the active ingredient plus any additional desired ingredient from a previously sterile-filtered solution thereof.

Pharmaceutical Compositions for Transdermal (Topical) Delivery

In some embodiments, the invention provides a pharmaceutical composition comprising an effective amount of a compound of Formula I or Formula II for transdermal delivery, and a pharmaceutical excipient suitable for transdermal delivery. Compositions of the present invention can be formulated into preparations in liquid, semi-solid, or solid forms suitable for local or topical administration. Examples of forms suitable for topical or local administration include but are not limited to, gels, water soluble jellies, creams, lotions, suspensions, foams, powders, slurries, ointments, oils, pastes, suppositories, solutions, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions comprising an effective amount of a compound of Formula I or Formula II also may comprise suitable solid or gel phase carriers, which are compounds that allow increased penetration of, or assist in the delivery of, therapeutic molecules across the stratum corneum barrier of the skin. There are many of these penetration-enhancing molecules known to those skilled in the art of topical formulation. Examples of such carriers and excipients include, but are not limited to, alcohols (e.g., ethanol), fatty acids (e.g., oleic acid), humectants (e.g., urea), glycols (e.g., propylene glycol), surfactants (e.g., isopropyl myristate and sodium lauryl sulfate), glycerol monolaurate, sulfoxides, pyrrolidones, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of the compounds of the present invention in controlled amounts, either with or without another agent. The construction and use of transdermal patches for the delivery of pharmaceutical agents is well known in the art. See, e.g., U.S. Pat. Nos. 5,023,252, 4,992,445 and 5,001,139, which are herein incorporated by reference.

Pharmaceutical Compositions for Inhalation.

In some embodiments, the invention provides a pharmaceutical composition comprising an effective amount of a compound of Formula I or Formula II for transdermal delivery, and a pharmaceutical excipient suitable for delivery by inhalation. Compositions for inhalation include solutions and suspensions in pharmaceutically acceptable, aqueous or organic solvents, or mixtures thereof, and powders. The liquid or solid compositions may contain suitable pharmaceutically acceptable excipients as described herein. The compositions may be administered by the oral or nasal respiratory route for systemic effect. In some embodiments, compositions in preferably pharmaceutically acceptable solvents may be nebulized by use of inert gases. In some embodiments, nebulized solutions may be inhaled directly from the nebulizing device. In other embodiments, nebulizing device may be attached to a face mask tent or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions comprising the compound of Formula I and/or II may also be prepared from compositions described herein and one or more pharmaceutically acceptable excipients suitable for buccal, sublingual, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Exemplary Treatment Regimens and Routes of Administration

Administration of each compounds or pharmaceutical composition of the present invention can be effected by any method that enables delivery of the compounds to the site of action. In some embodiments, the route of administration may be oral, by intraperitoneal injection, by inhalation, by transdermal infusion, or parenteral. The preferred route of administration is oral. In some cases, the oral administration may comprise administration of any of the oral dosage forms as described herein. The effective amount of the compound of Formula I or Formula II administered will be dependent on the subject being treated, the severity of the disorder or condition, the subject's risk of developing a demyelinating disorder, the rate of administration, the disposition of the compound and the discretion of the prescribing physician. However, an effective dosage is in the range of about 0.001 to about 1 mg per kg body weight per day, preferably about 0.01 to about 0.5 mg/kg/day, in single or divided doses. For a 70 kg human, this would amount to about 0.1 to about 64 mg/day, or about 2 to about 32 mg/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some cases, as for administration to humans, the oral dosage form may comprise 0.1, 0.5, 1, 2, 4, 8, 16, 24, 32, or 64 mg of the compound of Formula I and/or II. In preferred cases, the oral dosage form is a tablet. In some cases, the oral administration may comprise administration of a liquid formula.

In some embodiments, the route of administration is by injection. In some embodiments, the injection is intraperitoneal. In some embodiments, the route of administration is intravenous. In some embodiments, the injection is subcutaneous. In some embodiments, the injection is intramuscular. In some cases, as for administration to humans, the injection or injected dosage form may comprise 0.1, 0.5, 1, 2, 4, 8, 16, 24, 32, or 64 mg of the compound of Formula I and/or II.

In some embodiments, administration may comprise inhalation. In some cases, as for administration to humans, the inhaled dose or dosage form may comprise 0.1, 0.5, 1, 2, 4, 8, 16, 24, 32, or 64 mg of the compound of Formula I and/or II.

In some embodiments, administration may comprise infusion. In some cases, infusion may involve chronic, steady dosing. Devices for chronic, steady dosing, i.e.—by a controlled pump, are known in the art, (examples may be described in U.S. Pat. Nos. 7,341,577, 7,351,239, 8,058,251, herein incorporated by reference). In some cases, administration may comprise intracerebrovascular delivery. In some cases, administration may comprise intracerebral delivery. Methods for intracerebrovascular or intracerebral delivery are well known in the art, as disclosed by the following references, herein incorporated by reference: U.S. Pat. Nos. 5,711,316, 5,713,923, 5,735,814, 5,832,702, 5,836,935, 5,720,720, Chandler et al., Ann. N.Y. Acad. Sci., 531, 1988, pp. 206-212, Bouvier et al, Neurosurgery 20(2), 1987, pp. 286-291, Johnson et al., Ann. N.Y. Acad. Sci., 531, 1988, pp. 57-67, and Sendelbeck et al., Brain Res., 328, 1985, pp. 251-258, herein incorporated by reference. In some cases, administration may comprise direct injection into the spinal cord, for example, by epidural injection.

In some embodiments, one oral or injected dose for humans may be about 0.1 mg, about 0.5 mg, about 1 mg, about 2 mg, about 3 mg, about 4 mg, about 5 mg, about 6 mg, about 7 mg, about 8 mg, about 10 mg, about 12 mg, about 16 mg, about 32 mg, or about 64 mg. In some embodiments, one oral or injected dose for non-human subjects may be about 0.001 mg/kg, about 0.005 mg/kg, about 0.01 mg/kg, about 0.05 mg/kg, about 0.1 mg/kg, about 0.5 mg/kg, about 1 mg/kg, about 2 mg/kg, about 4 mg/kg, about 8 mg/kg, about 16 mg/kg, about 32 mg/kg, about 64 mg/kg. In some cases, an oral or injected dose may be administered about once per day, about twice per day, about 3-5 times per day, about once every other day, about once every two days, about twice a week, about once a week, about once every two weeks, about once a month, for as long as the subject is in need thereof.

One dose administered through intracerebrovascular delivery or intracerebral delivery may be about 50 ng, about 100 ng, about 200 ng, about 500 ng, about 1 µg, about 10 µg, about 25 µg, about 50 µg, about 100 µg, about 200 µg, about 500 µg, about 1 mg, about 5 mg, about 10 mg. In some cases, a dose may be administered about once per day, about once every other day, about twice a week, about once a week, about once every two weeks, about once a month, about once every 2-6 months, for as long as the subject is in need thereof.

In some cases, administration of guanabenz or its derivatives may commence for a subject in need thereof when the subject is first suspected of having a demyelinating disorder. In some cases, administration of guanabenz or its derivatives may commence for a subject in need thereof when the subject diagnosed with a demyelinating disorder. In some cases, administration of guanabenz or its derivatives may commence for a subject in need thereof before the onset of any symptoms of a demyelinating disorder, or after symptom onset. In some cases, administration of guanabenz or its derivatives may commence for a subject in need thereof after the subject has experienced a single isolated clinical symptom or symptoms. In some cases, administration of guanabenz or its derivatives may commence for a subject in need thereof when the subject is deemed to be at increased risk for developing a demyelinating disorder. In some cases, administration of guanabenz or one of its derivatives may commence for a subject in need thereof when the subject is in a remission phase of the disorder, for the purpose of preventing or reducing the severity of relapse. In some cases, a subject in remission may be administered guanabenz or one of its derivatives after symptom severity has reached a peak and has been in decline for at least one or two or several days.

Administration of the compound(s) of the invention may continue as long as necessary. In some embodiments, the compound(s) invention is administered for more than 1, 2, 3, 4, 5, 6, 7, 14, or 28 days. In some embodiments, the compound(s) invention is administered for more than 1 month, more than 2 months, more than 4 months, more than 6 months, more than 1 year, more than 2 years, more than 5 years. In some embodiments, the compound(s) of the invention is administered for less than for less than 1 month, less than 2 months, less than 4 months, less than 6 months, less than 1 year, less than 2 years, less than 5 years. In some embodiments, the compound(s) of the invention is administered for less than 28, 14, 7, 6, 5, 4, 3, 2, or 1 day. In some embodiments, an agent of the invention is administered chronically on an ongoing basis, e.g., for the treatment or prevention of a demyelinating disorder.

The compounds of the invention may be administered in dosages. It is known in the art that due to inter-subject variability in compound pharmacokinetics, individualization and/or adjustment of the dosing regimen may be necessary for optimal therapy.

In some cases, the timing of dosing may be chosen in order to minimize potential side-effects from the compounds of the invention. For example, the compounds of the invention may, in some instances, induce drowsiness in a subject. In some embodiments, a dose of a compound of the invention is provided in the evening, in order to minimize the effect of drowsiness on the activities of the subject which, in turn, may allow a higher dose to be administered to the subject in a single dosage. In some embodiments, a single dose of about 64 mg of a compound of the invention is administered in the evening. As used herein, the term "evening" generally refers to a time after about 5:00 pm, after about 6:00 pm, after about 7:00 pm, after about 8:00 pm, after about 9:00 pm, after about 10:00 pm, or after about 11:00 pm. In some embodiments, a compound of the invention may be administered with another compound that counteracts drowsiness, such as a stimulant.

Exemplary Combination Therapies

In some aspects of the present invention, the compounds described herein can also be used in combination with other known agents that are selected for their therapeutic value to the subject in need thereof. In some aspects of the present invention, the compound(s) described herein may be used in a combination therapy which comprises one or more additional agents known to modulate other pathways, or other components of the same pathways as that modulated by the compound(s), or the same targets of the same pathway modulated by the compound(s). Examples of pathways or pathway components modulated by the compound(s) described herein and may also be targeted by the one or more additional agents include, but are not necessarily limited to, ER stress pathways, PERK pathways, eIF2α, phosphorylated eIF2α, GADD34, protein phosphatase I (PPI), ATF4, IRE1 pathways, ATF6 pathways. Examples of other pathways or pathway components that may be targeted by the one or more additional agents include, but are not limited to: pathways related to immune function, immunomodulatory pathways, inflammatory pathways, cytokine pathways, T cells, T cell proliferation pathways, CD4+ T cells, Treg cells, CD8+ T cells, Major Histocompatibility Complex (MHC), antigen presenting cells (APC), adhesion molecule, MMP and/or chemokine expression, leukocytes, leukocyte migration across the BBB, α4 integrins, lymphocytes, monocytes, topisomerase-2, macrophages, B cells, B or T lymphocytes, interleukins, TNF-α, interferons (IFN), IFN-β, IFN-γ, neurotrophic pathways, neurotrophic factors such as, e.g., NGF, BDNF, NT-3, CNTF, neuroprotective pathways, immune tolerance to myelin or myelin-associated proteins, antibody production, etc., apoptosis, protein folding, chaperones, heat shock proteins, etc. Of particular interest are agents known to be useful for the treatment of demyelinating disorders.

In some embodiments of the use of the compounds described herein for combination therapy, other agents may be administered in the same pharmaceutical composition. In some embodiments of the use of the compounds described herein for combination therapy, other agents do not have to be administered in the same pharmaceutical composition, but may be administered simultaneously with the composition of the compound(s) described herein. In other embodiments of the use of the compounds described herein for combination therapy, the other agents may be administered at different times. In some embodiments, because of differences in physical and chemical characteristics of the compound(s) described herein and the other agents, the compound(s) and other agents may be administered by different routes. The determination of the mode of administration and the advisability of administration in the same pharmaceutical composition is well within the knowledge of one skilled in the art, e.g., a physician. The initial co-administration can be made according to established protocols known in the art, and then, based upon the observed effects, the dosage, modes of administration and times of administration can be modified by the skilled clinician.

In some embodiments, it may be appropriate to administer at least one of the compounds described herein in combination with another therapeutic agent. In a non-limiting example, if a subject is experiencing a side effect from administration of one of the compounds described herein (such as, for example, drowsiness), then it may be appropriate to administer an anti-drowsiness agent in combination with the compound. Alternatively, by way of another non-limiting example, the therapeutic effectiveness of one of the compounds described herein may be enhanced by administration of an adjuvant (wherein the adjuvant may have minimal therapeutic benefit, but in combination with another therapeutic agent such as the compound(s) described herein, the overall therapeutic benefit to the patient is enhanced). In another non-limiting example, the therapeutic benefit to a subject may be increased or enhanced by a combination therapy of one of the compounds described herein with one or more additional therapeutic agents that also has therapeutic benefit. In some embodiments, the overall benefit experienced by the patient from the combination therapy may be an additive effect of the individual agents. In some embodiments, the subject may experience a synergistic benefit from the combination therapy.

One of skill in the art will appreciate that therapeutically effective dosages may vary when the agents are used in combination therapy. Methods for determining therapeutically effective dosages of drugs and other agents for use in combination therapy regimens are known to those of skill in the art.

It is understood by those of skill in the art that the combination therapy regimen for the subject in need thereof can be modified in accordance with a variety of factors. These factors may include, but are not limited to, the demyelinating disorder from which the subject suffers from or is at increased risk for, any other medical condition experienced by the subject, as well as the age, weight, sex, diet, and medical history of the subject. Thus, the combination therapy regimen actually employed can vary widely and therefore can deviate from exemplary combination therapies described herein.

Additional agents useful for combination therapy include any agents capable of modulating a target molecule implicated in a demyelinating disorder, either directly or indirectly. Non-limiting examples of target molecules modulated by additional agents include enzymes, enzyme substrates, antibodies, antigens, membrane proteins, products of transitions, nuclear proteins, lipid rafts, cytosolic proteins, mitochondrial proteins, lysosomal proteins, scaffold proteins, phosphoproteins, glycoproteins, nuclear receptors, membrane receptors, G-protein-coupled receptors, nuclear receptors, protein tyrosine kinases, protein serine/threonine kinases, phosphatases, proteases, hydrolases, lipases, phospholipases, ligases, reductases, oxidases, synthases, transcription factors, ion channels, RNA, DNA, RNAse, DNAse, phospholipids, sphingolipids, ion channel proteins, nucleotide-binding proteins, calcium-binding proteins, chaperones, DNA binding proteins, RNA binding proteins, scaffold proteins, tumor suppressors, cell cycle proteins, and histones.

Additional agents may be: small molecules, nutraceuticals, vitamins, e.g., vitamin D, drugs, pro-drugs, biologics, peptides, peptide mimetics, antibodies, antibody fragments, cell or tissue transplants, vaccines, polynucleotides, DNA molecules, RNA molecules, (i.e.—siRNA, miRNA), antibodies conjugated to drugs, toxins, fusion proteins. Agents may be delivered by vectors, including but not limited to: plasmid vectors, viral vectors, non-viral vectors, liposomal formulations, nanoparticle formulations, toxins, therapeutic radioisotopes, etc.

In some embodiments, the compound(s) of the present invention may be useful in combination therapy with one or more agents that are currently approved by the FDA for the treatment or prophylaxis of a demyelinating disorder. Examples of other agents approved by the FDA for treatment or prophylaxis of demyelinating disorders include, but are not limited to, interferon β, IFN β-1a (brand names: AVONEX, REBIF), IFNβ-1b (brand name: BETASERON), glatiramer acetate (COPAXONE, Copolymer-1), natalizumab (TYSABRI), mitoxantrone ($C_{22}H_{28}N_4O_6 \cdot 2HCl$), methylprednisone, methylprednisolone, thalidomide, fingolimod (GILENIA), dimethyl fumarate (BG-12), teriflunomide (AUBAGIO), anti-LINGO antibody, alemtuzumab (CAMPATH), dalfampridine, PEG-interferon beta-1a (BIIB017), daclizumab (ZENAPAX), laquinimod, and ocrelizumab. Accordingly, a method of the invention may comprise administering to a subject a compound of the present invention with one or more additional therapeutic agent useful in the treatment and/or prophylaxis of a demyelinating disorder. Compound(s) of the present invention may be administered before, after, or concurrently with the one or more additional therapeutic agents. In some embodiments, compound(s) of the present invention may be formulated in a composition comprising a pharmaceutically acceptable carrier and the one or more additional therapeutic agents. In one embodiment, the compound(s) of the present invention are administered in combination with glatiramer acetate (COPAXONE). In one embodiment, the compound(s) of the present invention are administered in combination with dimethyl fumerate. In one embodiment, the compound(s) of the present invention are administered in combination with fingolimod. In one embodiment, the compound(s) of the present invention are administered in combination with interferon beta-1a. In one embodiment, the compound(s) of the present invention are administered in combination with interferon beta-1b. In one embodiment, the compound(s) of the present invention are administered in combination with mitoxantrone. In one embodiment, the compound(s) of the present invention are administered in combination with natalizumab. In one embodiment, the compound(s) of the present invention are administered in combination with dalfampridine. In one embodiment, the compound(s) of the present invention are administered in combination with daclizumab. In some embodiments the compound is guanabenz. In some embodiments, the formulation may be a formulation for injection. In some embodiments the formulation may be a formulation for subcutaneous administration. In some embodiments the formulation may be a formulation for intravenous administration.

In some embodiments, the compound(s) of the present invention may be useful in combination therapy with other agents that are associated with altered clinical outcomes of a demyelinating disorder but not FDA approved for the treatment of the disorder. Examples of other agents associated with altered clinical outcomes of a demyelinating disorder but not approved for treatment of the disorder include, but are not limited to, cyclophosphamide, methotrexate, azathioprine, cyclosporine, etc.

In some embodiments, the compound(s) of the present invention may be useful in combination therapy with other agents that are associated with neuroprotection or axonal regeneration. Examples of such agents include, but are not limited to, neurotrophic factors (e.g., NT-3, BDNF, NGF, CTNF, FGF, GDNF), MANF polypeptides, stem cell transplantation therapy (e.g., transplantation of hematopoietic and non-hematopoietic stem cells, agents that target pathways associated with neurodegeneration (e.g., ubiquitin-proteasome pathways, ER stress pathways, autophagy pathways, mitochondrial pathways, oxidative stress pathways, apoptosis pathways, etc.). Further examples of pathways, pathway components, or agents that may promote axonal regeneration include, but are not limited to, PirB pathways, Nogo receptor pathways, netrin, bone morphogenic protein/Smad1 pathways, cAMP, Vitamin D, among others.

In some embodiments, the compound(s) of the present invention may be useful in combination therapy with other agents that are useful for reducing or preventing damage induced by inflammation. Examples of such agents include but are not necessarily limited to; steroidal anti-inflammatory drugs, non-steroidal anti-inflammatory drugs, immune selective anti-inflammatory drugs, cyclooxygenase (COX) inhibitors, prostaglandin inhibitors, herbs with anti-inflammatory qualities (e.g., Harpagophytum, hyssop, ginger, turmeric, *Arnica montana*, sesquiterpene lactone, willow bark), among others.

In some embodiments, the compound(s) of the present invention may be useful in combination therapy with other agents that are useful for the treatment of pain and/or inflammation symptoms that may be associated with a demyelinating disorder. Examples of such agents include, but are not limited to, analgesics, histamine, histamine antagonists, bradykinin, bradykinin antagonists, agents that modulate 5-hydroxytryptamine (serotonin) pathways, serotonin reuptake inhibitors, serotonin-norepinephrine reuptake inhibitors, tricyclic antidepressants, gamma-aminobutyric acid analogs, gamma-aminobutyric acid receptor agonists, benzodiazapenes, narcotics, eicosanoids, prostaglandins, thromboxanes, leukotrienes, aspirin, anti-inflammatory agents, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, agents that target cytokines which mediate interactions involved in humoral and cellular immune responses, lipid-derived autacoids, β-adrenergic agonists, ipratropium, glucocorticoids, methylxanthines, sodium channel blockers, opioid receptor agonists, cannabinoid receptor agonists, *cannabis*, calcium channel blockers, membrane stabilizers, acetaminophen, ibuprofen, aspirin, leukotriene inhibitors, any combinations thereof, or others. In other embodiments, the compound(s) of the present invention may be useful in combination therapy with other treatments for pain that do not comprise an additional agent, e.g., meditation therapy, massage therapy, psychological therapy.

In some embodiments, the compound(s) of the present invention may be useful in combination therapy with other agents that are useful for the treatment of other somatosensory disturbances associated with a demyelinating disorder (e.g., tingling, numbness). Examples of such agents include, but are not limited to, neurotrophin-3, antidepressants, anti-epileptic drugs, synthetic cannabinoids, pregabalin, gabapentin, sodium valproate, among others. In other embodiments, the compound(s) of the present invention may be useful in combination therapy with other treatments for somatosensory disturbances that do not comprise an additional agent, e.g., transcutaneous electrical nerve stimulation, meditation therapy, psychological therapy.

In some embodiments, the compound(s) of the present invention may be useful in combination therapy with other agents that are useful for the treatment of motor dysfunction associated with a demyelinating disorder. Examples of such agents include, but are not limited to, gamma-aminobutyric acid analogs, gamma-aminobutyric acid receptor agonists, benzodiazepines (e.g., clonazepam, carbamazepine), muscle relaxants, baclofen, anticholinergics, anticonvulsants (e.g., sodium valproate, phenytoin), anti-Parkinsonian agents (e.g., levadopa), antipsychotic agents (e.g., risperidone). In other embodiments, the compound(s) of the present invention may be useful in combination therapy with other treatments for motor dysfunction that do not comprise an additional agent, e.g., chiropractic neurology, motor training, e.g., rehearsal by eye movement, deep brain stimulation.

In some embodiments, the compound(s) of the present invention may be useful in combination therapy with other agents that are useful for the treatment of fatigue symptoms that may be associated with a demyelinating disorder. Examples of such agents include, but are not limited to, iron supplements for anemia, medications and/or machines to help sleep apnea, sleeping pills, medications to control blood sugar levels, medications to regulate thyroid function, antibiotics, vitamins, nutraceuticals (e.g., gingko *biloba*), antidepressants. In other embodiments, the compound(s) of the present invention may be useful in combination therapy with other treatments for fatigue that do not comprise an additional agent, e.g., sleep therapy, meditation therapy, diet or exercise changes, psychological therapy.

In some embodiments, the compound(s) of the present invention may be useful in combination therapy with other agents that are useful for the treatment of depression or other mood disorders that may be associated with a demyelinating disorder. Examples of such agents include, but are not limited to, tricyclic antidepressants, tetracyclic antidepressants, selective serotonin reuptake inhibitors, serotonin/norepinephrine reuptake inhibitors, monoamine oxidase inhibitors, opioids (e.g., buprenorphine), amphetamines, antipsychotics, benzodiazepines, nutraceuticals (e.g., St. John's Wort extract, Salvia elegans, Salvia sclarea), tryptophan, omega 3 fatty acids, among others. In other embodiments, the compound(s) of the present invention may be useful in combination therapy with other treatments for fatigue that do not comprise an additional agent, e.g., sleep therapy, meditation therapy, diet or exercise changes, psychological therapy, electroconvulsive therapy.

In some embodiments, the compound(s) of the present invention may be useful in combination therapy with other agents that are useful for the treatment of cognitive dysfunction that may be associated with a demyelinating disorder. Examples of such agents include, but are not limited to, IFN-β 1a, IFN-β 1b, physostigmine, acetylcholinesterase inhibitors (e.g., donepezil), nutraceuticals (e.g., gingko biloba), among others. In other embodiments, the compound(s) of the present invention may be useful in combination therapy with other treatments for cognitive dysfunction that do not comprise an additional agent, e.g., cognitive retraining, psychological intervention, attention-training tasks, etc.

In some embodiments, the compound(s) of the present invention may be useful in combination therapy with other agents that are useful for the treatment of sexual dysfunction that may be associated with a demyelinating disorder. Examples of such agents include, but are not limited to, vasoactive agents used for the treatment of erectile dysfunction (e.g., phenoxybenzamine phentolaimine, papverine, prostaglandin E1, vasoactive intestinal polypeptide, cyclic guanosine 3',5',-monophosphate diesterase inhibitors such as sildenafil (Viagra), Tadalafil, Vardenafil, testosterone therapy), agents used for the treatment of female sexual dysfunction (e.g., estrogen therapy, androgen therapy). In other embodiments, the compound(s) of the present invention may be useful in combination therapy with other treatments for sexual dysfunction that do not comprise an additional agent, e.g., changing lifestyle habits, meditation, yoga, psychological counseling, etc.

In some embodiments, the compound(s) of the present invention may be useful in combination therapy with other treatments useful for the management of bladder or bowel dysfunction that may be associated with a demyelinating disorder. Examples of such treatments include: functional electrical stimulation, which may comprise implantation of an electrical stimulator that regulates the coordinated activation of muscles/nerves controlling the bladder or bowel sphincter.

Encompassed in aspects of the present invention is the use of a therapeutically effective amount of a compound of Formula I and/or II and one or more additional agents to be used in combination therapy. Also included in the subject methods is the use of a sub-therapeutic amount of a compound of Formula I and/or II and/or a sub-therapeutic amount of one or more additional agents. The individual components of the combination, though present in sub-therapeutic amounts, may synergistically yield an efficacious effect and/or reduced adverse effects in an intended application.

In addition, the compounds described herein may also be used in combination with other treatments not involving administration of an additional agent, that may provide additional or synergistic benefit to the patient. In one non-limiting example, subjects may experience improved therapeutic and/or prophylactic benefit in the methods described herein, wherein pharmaceutical composition of a compound disclosed herein and/or combinations with other therapeutics are combined with psychiatric or psychological therapy sessions (e.g., talk therapy sessions).

EXAMPLES

Figure 2A:
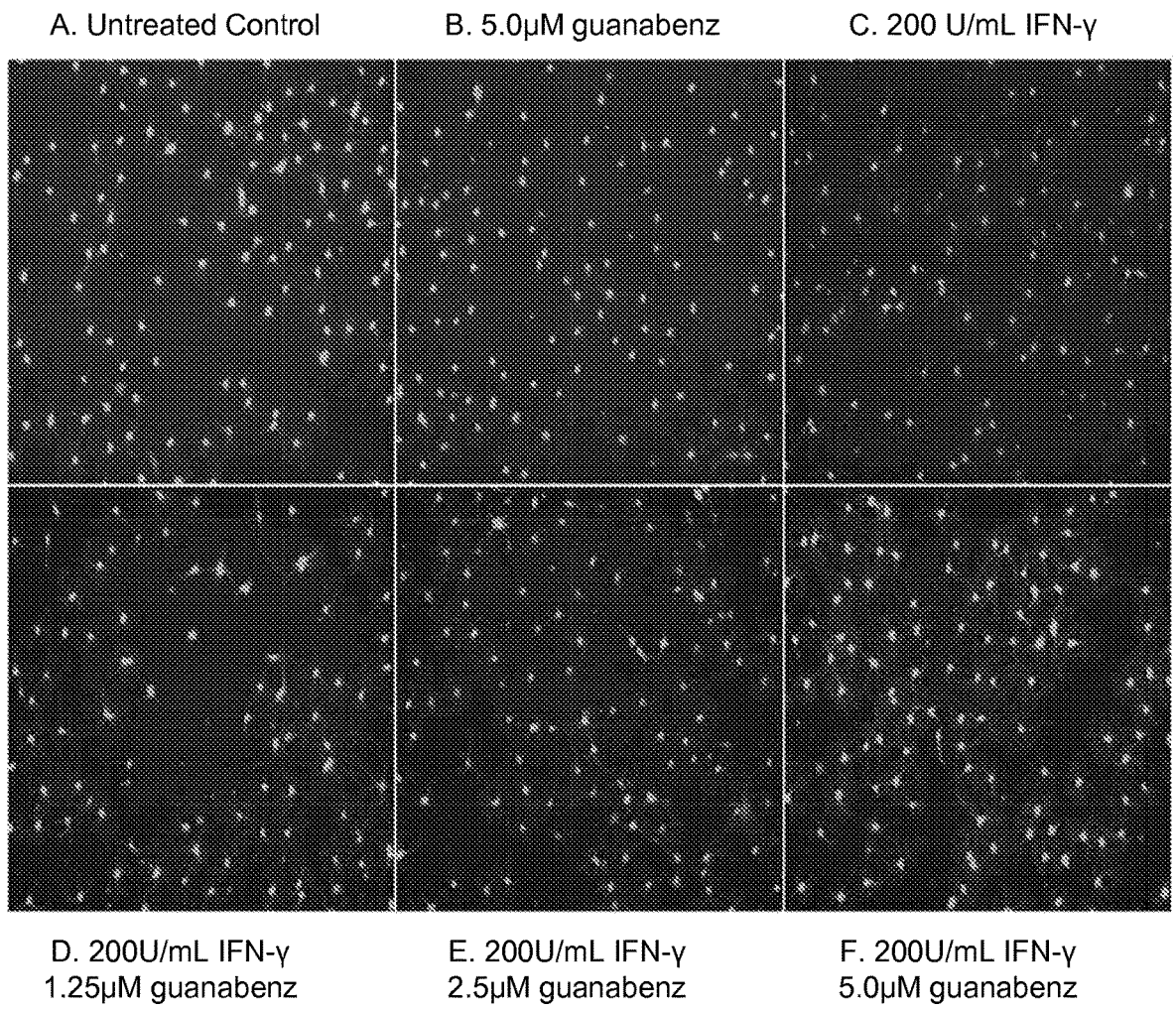
FIG. 2A depicts photomicrographs of a fluorescein-diacetate/propidium iodide assay for cell viability in differentiating rat oligodendrocyte precursor cells (drOPCs) treated with interferon-gamma (IFN-γ) alone or in combination with guanabenz, where green cells are viable cells and red cells are non-viable cells.
Figure 2B:
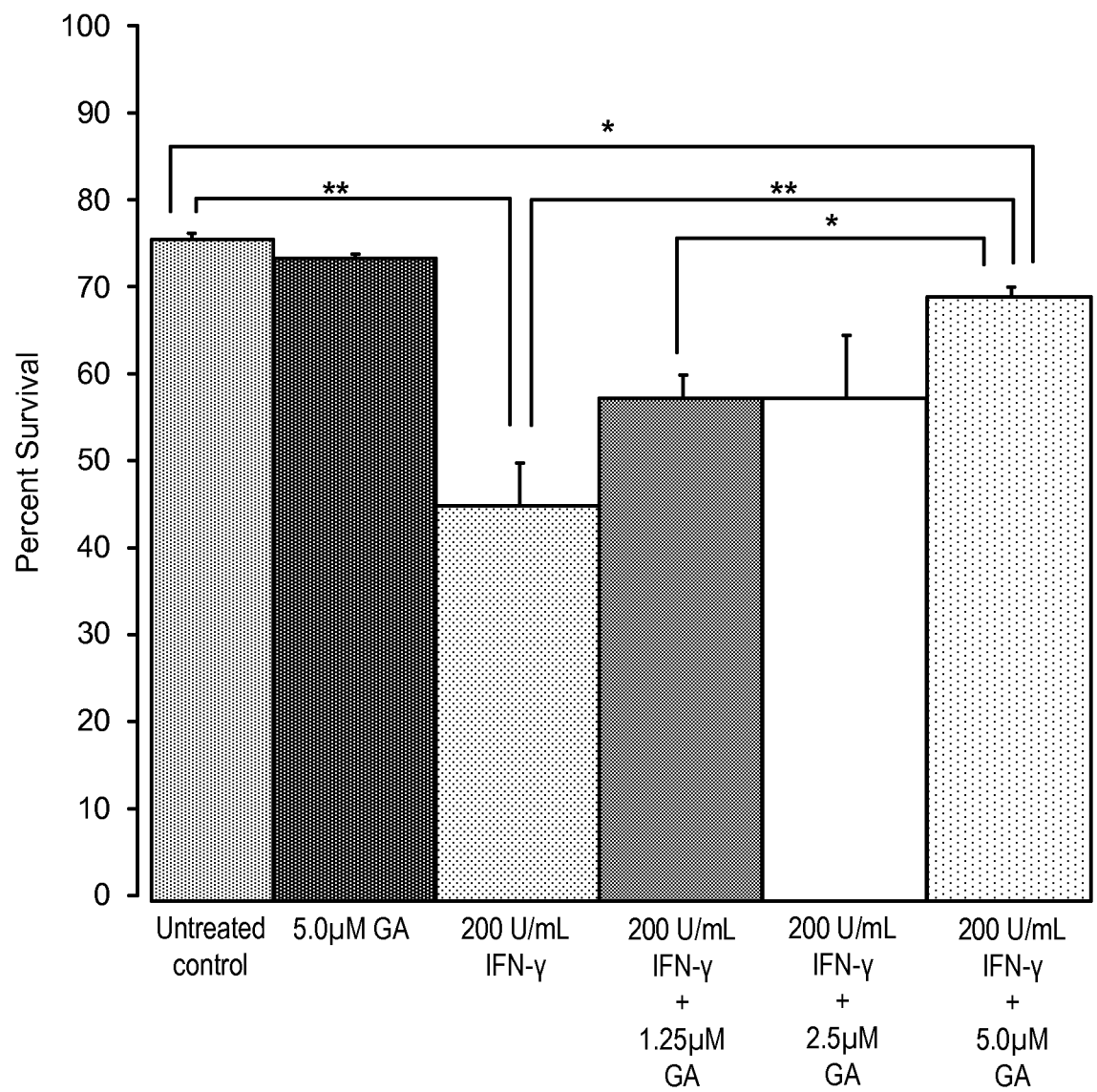
FIG. 2B illustrates the quantitation of the results shown in FIG. 2A.

Example 1 guanabenz protects differentiating rat oligodendrocyte precursor cells (drOPCs) against interferon-γ induced cell death (FIG. 2A). Interferon-γ is an inflammatory cytokine that is thought to contribute to multiple sclerosis exacerbations, therefore, treatment of cultured cells of the oligodendrocyte lineage with interferon-γ provides a useful cellular model of MS-related inflammation. drOPCs were isolated and purified to >95% homogeneity from 6-7 day old Sprague-Dawley rat cortices by immunopanning as previously described (Chan et al. 2004 Neuron 43:2; 183-191). Briefly, rat cortices were extracted, diced, and digested with papain at 37° C. Cells were then triturated and resuspended in panning buffer containing insulin, then sequentially immunopanned at room temperature on three plates containing Ran-2, GalC, and O4 antibodies from hybridomal supernatant. The remaining $O4^+GalC^-$ OPCs were removed from the plates with trypsin, resuspended in growth media, and seeded at 37° C. onto pDL-coated flasks to facilitate proliferation. Once sufficient numbers were reached, OPCs were split, plated in differentiation media at 200,000 cells/well, and allowed to differentiate for 24 hours. Differentiation media was then removed and replaced with treatment media (containing IFN-γ (EMD Chemicals, Gibbstown, N.J.) and/or guanabenz (MP Biomedicals, Solon, Ohio)) which was refreshed after 24 hours. Following 48 hours of treatment, media was removed and the cells were incubated in FDA/PI (fluorescein-diacetate/propidium iodide) for 3 minutes, rinsed with 1×PBS, and imaged for live/dead cell quantification. In living cells, non-fluorescent FDA is converted into fluorescein, giving off a bright green fluorescence. PI is membrane impermeable and therefore excluded from live cells. Therefore, green cells indicate viable cells and red cells indicate non-viable cells. Both control drOPCs not exposed to IFN-γ and 5.0 μM guanabenz-alone treated samples exhibit similar numbers of green and red cells, indicating that guanabenz alone does not impact cell viability (A,B). Treatment with 200 U/ml IFN-γ alone reduced the number of green cells and increased the number of red cells (C). Co-application of 1.25 μM and 2.5 μM guanabenz partially restored viability (D, E), while 5.0 μM guanabenz increased the green/red cell ratio back to control levels (F), indicating guanabenz protects cells against IFN-γ induced cell death. FIG. 2B illustrates the quantitation of the experiment in FIG. 2a. Both untreated control and guanabenz treated samples exhibit comparable percent survival. Treatment with IFN-γ alone caused a roughly 40-50% decrease in cell survival. Co-application of 1.25 and 2.5 μM guanabenz increased cell survival by roughly 25% compared to IFN-γ alone samples, and 5.0 μM guanabenz increased survival almost to control levels. Data is presented as the mean+/−SEM for an N=3/group. (*p<0.05, **p<0.005)

Figure 3A:
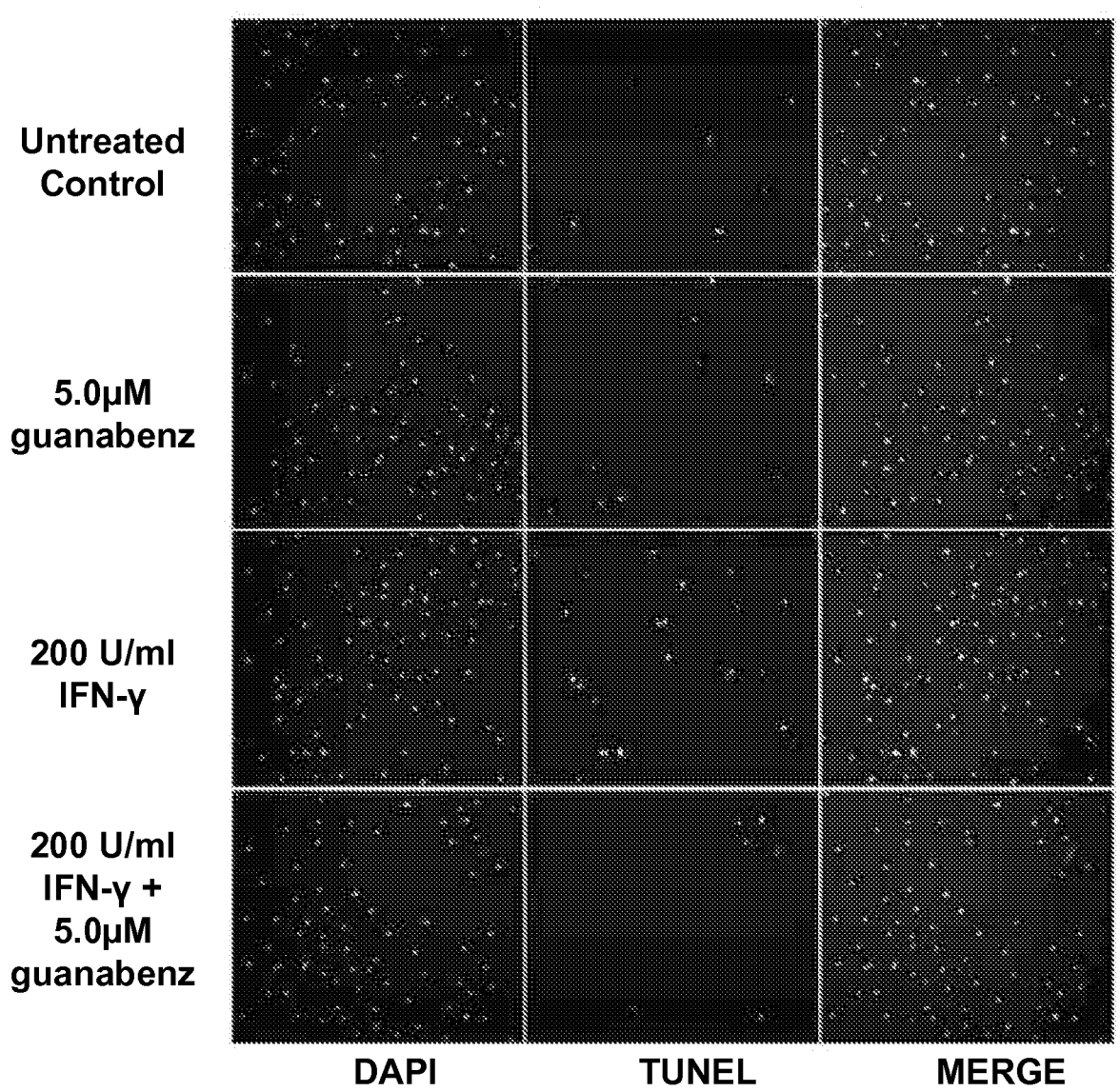
FIG. 3A depicts photomicrographs of a TUNEL assay for apoptosis in drOPCs treated with interferon-gamma (IFN-γ), alone or in combination with guanabenz.

Example 2 guanabenz protects differentiating rat oligodendrocyte precursor cells (drOPCs) against interferon-γ induced apoptosis (FIG. 3A). Cells were isolated as described previously and plated in chamber slides at 20,000 cells/chamber. Cells were then treated with the same IFN-γ and guanabenz protocol as described previously, then subjected to a TUNEL assay. Treatment with IFN-γ alone caused a significant increase in apoptosis (as indicated by the increased numbers of green fluorescent cells), but co-treatment with 5.0 μM guanabenz reduced IFN-γ induced apoptosis.

Figure 3B:
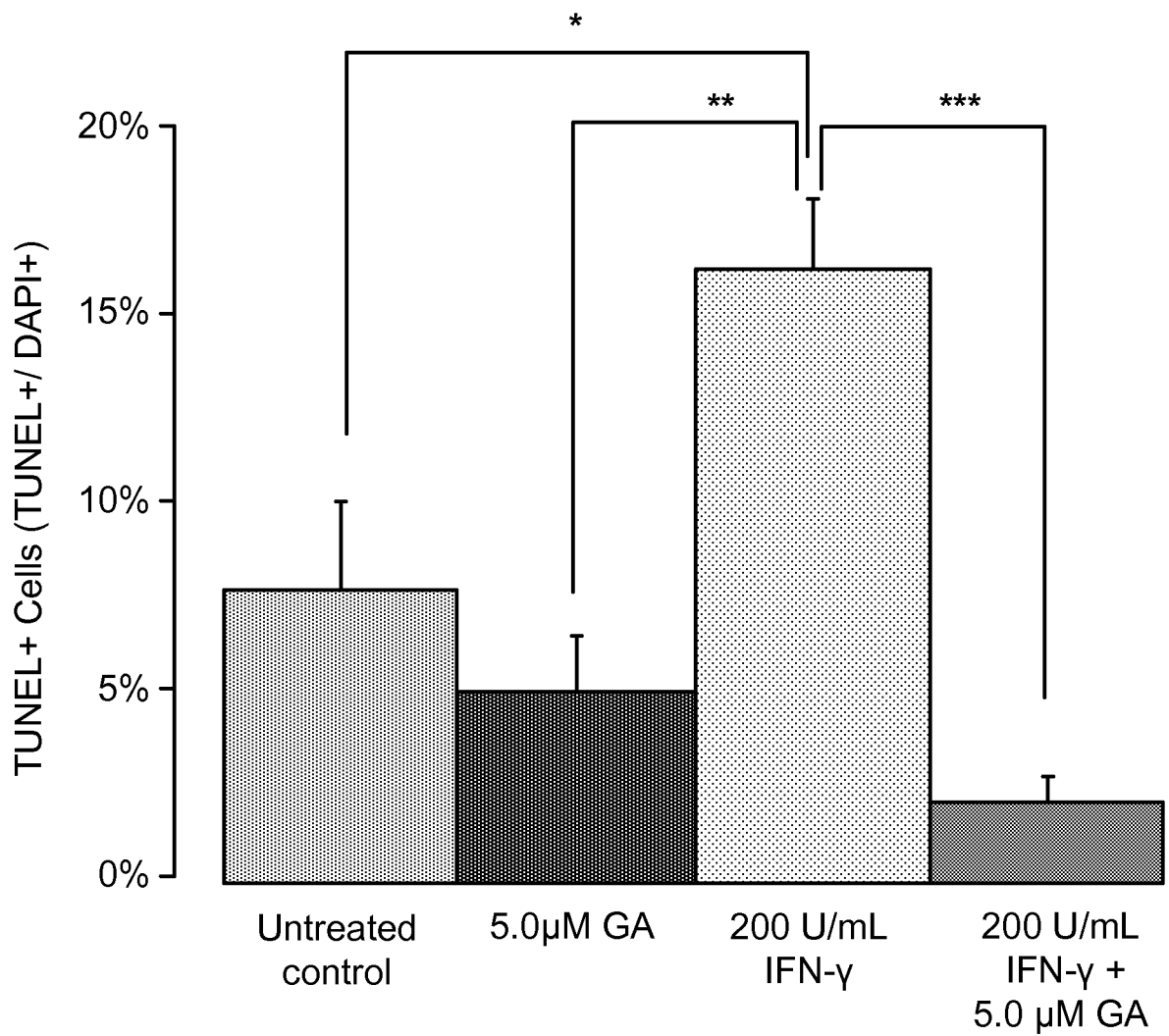
FIG. 3B illustrates the quantitation of the results shown in FIG. 3A.

FIG. 3B illustrates the quantitation of the experiment in FIG. 3a. Treatment with IFN-γ alone caused a significant (2-3 fold) increase in apoptosis compared to control cells, but co-treatment with 5.0 μM guanabenz reduced IFN-γ induced apoptosis by about 87.5% compared to IFN-γ alone. Error bars represent mean±SEM for an N=3/group (*p<0.05, p<0.005, *p<0.0005)

Figure 4:
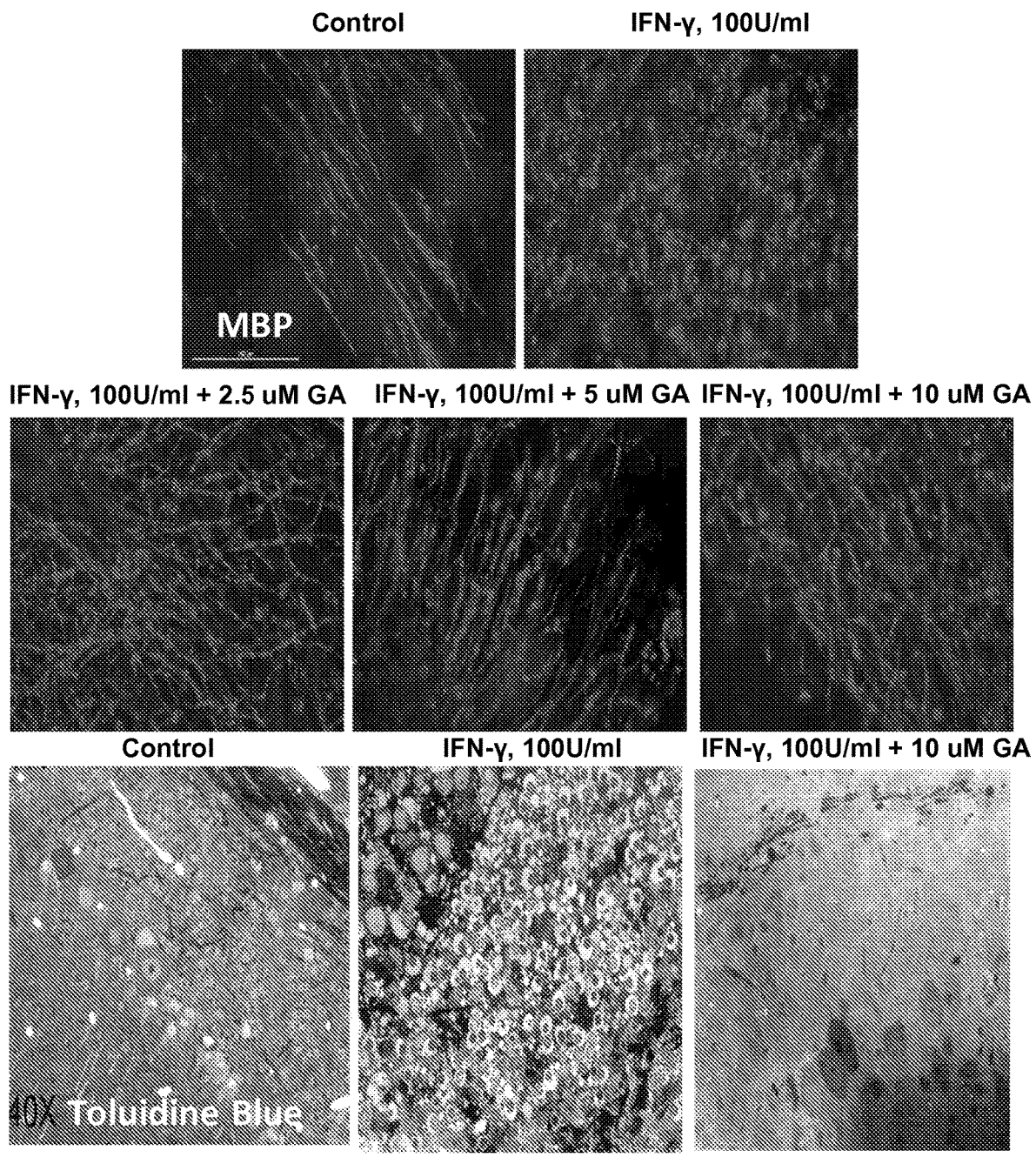
FIG. 4 depicts cultured rat cerebellar slices stained for myelin basic protein and toluidine blue. The depicted rat cerebellar samples were treated with IFN-γ alone or in combination with 2.5-10 μM guanabenz.

Example 3 immunohistochemical analysis of myelin basic protein and toluidine blue staining demonstrates that guanabenz preserves myelin fibers and neuronal cytoarchitecture in ex vivo cultured cerebellar slices (FIG. 4). Briefly, cerebellar sections were prepared from 6 day old Sprague-Dawley rat pups. Whole brains were extracted and embedded in 2% agarose in 1×PBS before cerebellar sections, including brain stem, were sectioned at a thickness of 300 μm via vibratome. Two to three sections were collected per well and grown in growth media with Fungizone. Sections were then switched to heat inactivated growth media and treated with 100 U/ml IFN-γ and or guanabenz for seven days, with half the volume of media, including treatments, refreshed daily. Sections were then stained for myelin-basic protein (A-E) and toluidine blue (F-H), used to visualize myelin and neuronal cytoarchitecture. Untreated sections exhibit long, intact myelin fibers, while IFN-γ treated sections exhibit fragmented structure, indicative of degenerated myelin fibers and axonal degeneration. Co-application of 2.5 μM, 5.0 μM, and 10.0 μM guanabenz restored intact, long myelin fiber and axonal structure in IFN-γ-treated sections.

Figure 5A:
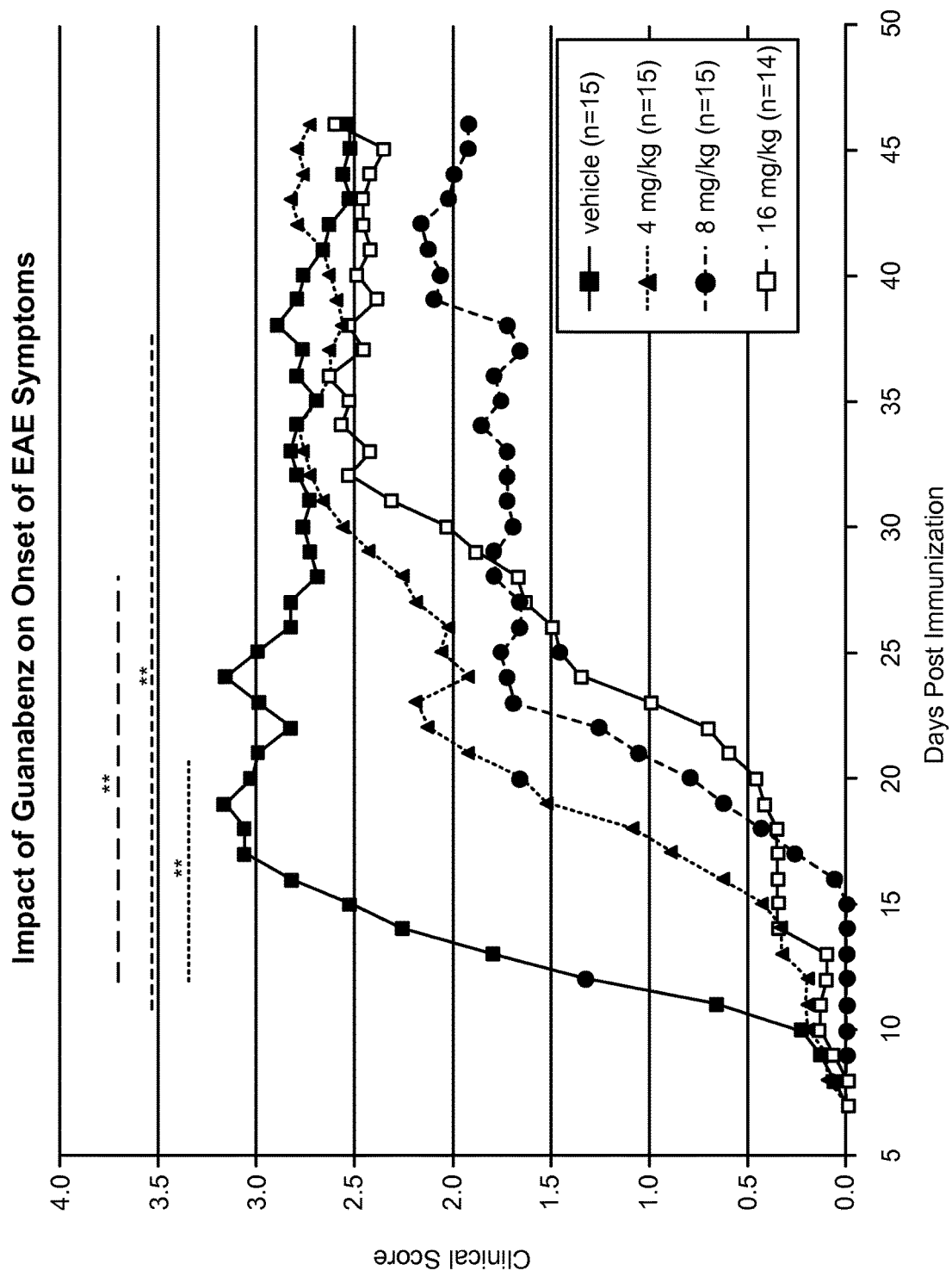
FIG. 5A depicts clinical scores over the course of experimental autoimmune encephalitis (EAE), a mouse model of chronic multiple sclerosis. The mice were treated with 4-16 mg/kg/day of guanabenz or with control vehicle.
Figure 5B:
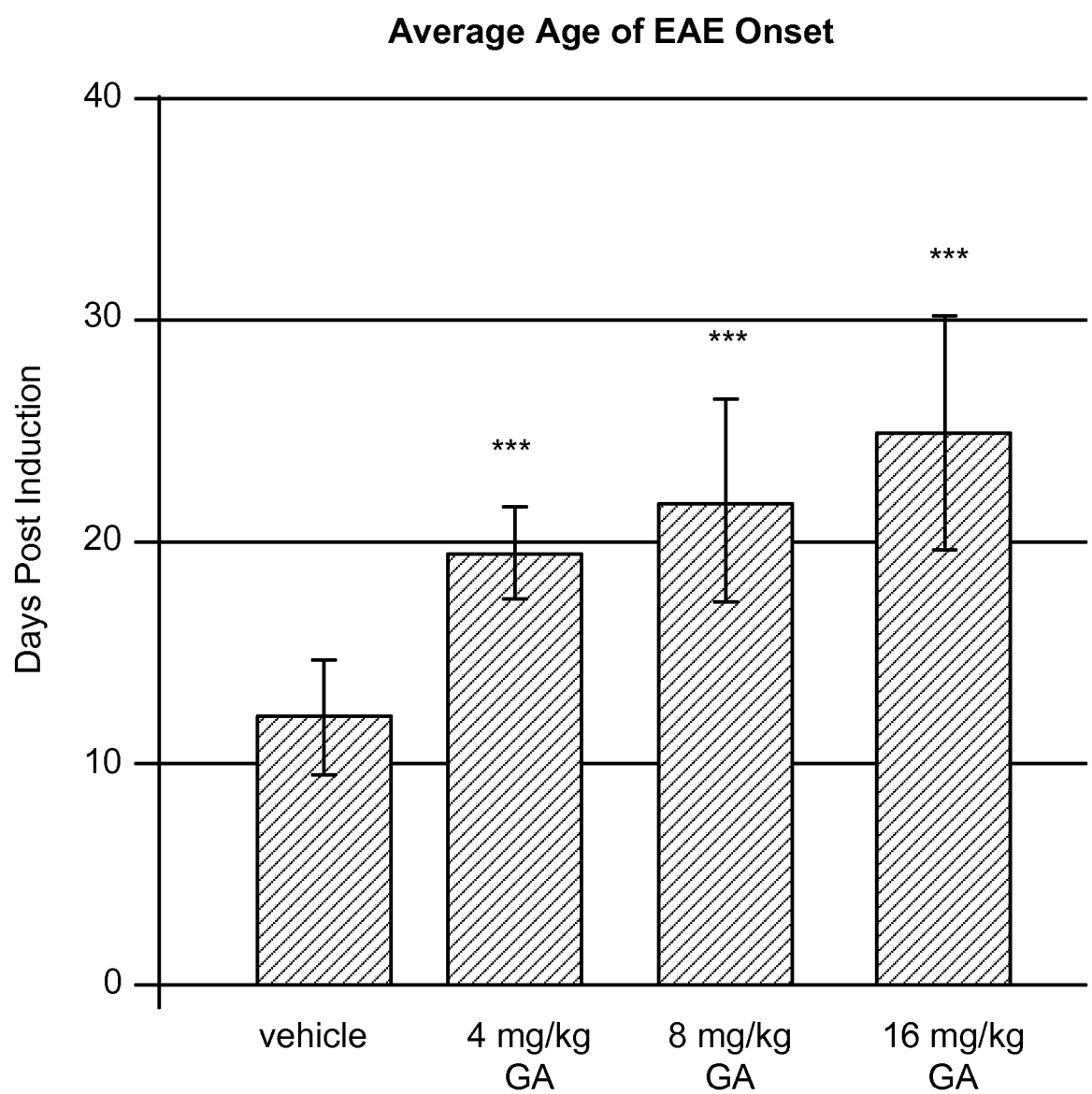
FIG. 5B depicts average age of symptom onset over the course of experimental autoimmune encephalitis (EAE), a mouse model of chronic multiple sclerosis. The mice were treated with 4-16 mg/kg/day of guanabenz or with control vehicle.

Example 4 guanabenz delays symptom onset in an in vivo mouse model of chronic progressive multiple sclerosis (FIGS. 5A and 5B). Subcutaneous injections of 200 μg myelin oligodendrocyte glycoprotein (MOG) 35-55 peptide emulsified in complete Freund's adjuvant (BD Biosciences, San Jose, Calif.) supplemented with 200 μg of *Mycobacterium tuberculosis* (strain H37Ra; BD Biosciences) were injected into the lower flanks of 8 week old female C57BL/6J mice (Jackson Laboratory, Bar Harbor, Me.). Two intraperitoneal (IP) injections of 400 ng pertussis toxin each (List Biological Laboratories, Denver, Colo.) were administered 0 and 48 h later. Mice were monitored for clinical symptoms beginning post-immunization day 7 (PID 7) and scored daily (0=healthy, 1=flaccid tail, 2=ataxia and/or paresis of hindlimbs, 3=paralysis of hindlimbs and/or paresis of forelimbs, 4=tetraparalysis, 5=moribund or death). Mice were treated intraperitoneally with guanabenz or vehicle (sterile 0.9% NaCl) daily beginning PID 7. All protocols were approved by the University of Chicago Institutional Animal Care and Use Committee. Vehicle-treated subjects exhibited rapid onset of symptoms (FIG. 5A). All guanabenz doses resulted in a significant delay in symptom onset (FIG. 5A). Note: bright red dots indicate average age of onset. N=14-15/group. (p<0.005) FIG. 5B depicts quantitation of EAE onset from the experiment described in FIG. 5a. Vehicle administered subjects exhibited an average symptom onset of about 12 days. By contrast, treatment with 4 mg/kg/day guanabenz delayed symptom onset 19 days, 8 mg/kg/day guanabenz delayed symptom onset to about 22 days, and 16 mg/kg/day guanabenz delayed symptom onset to about 25 days. Error bars represent mean±SD for an N=14-15/group. (*p≤0.0005).

Figure 6:
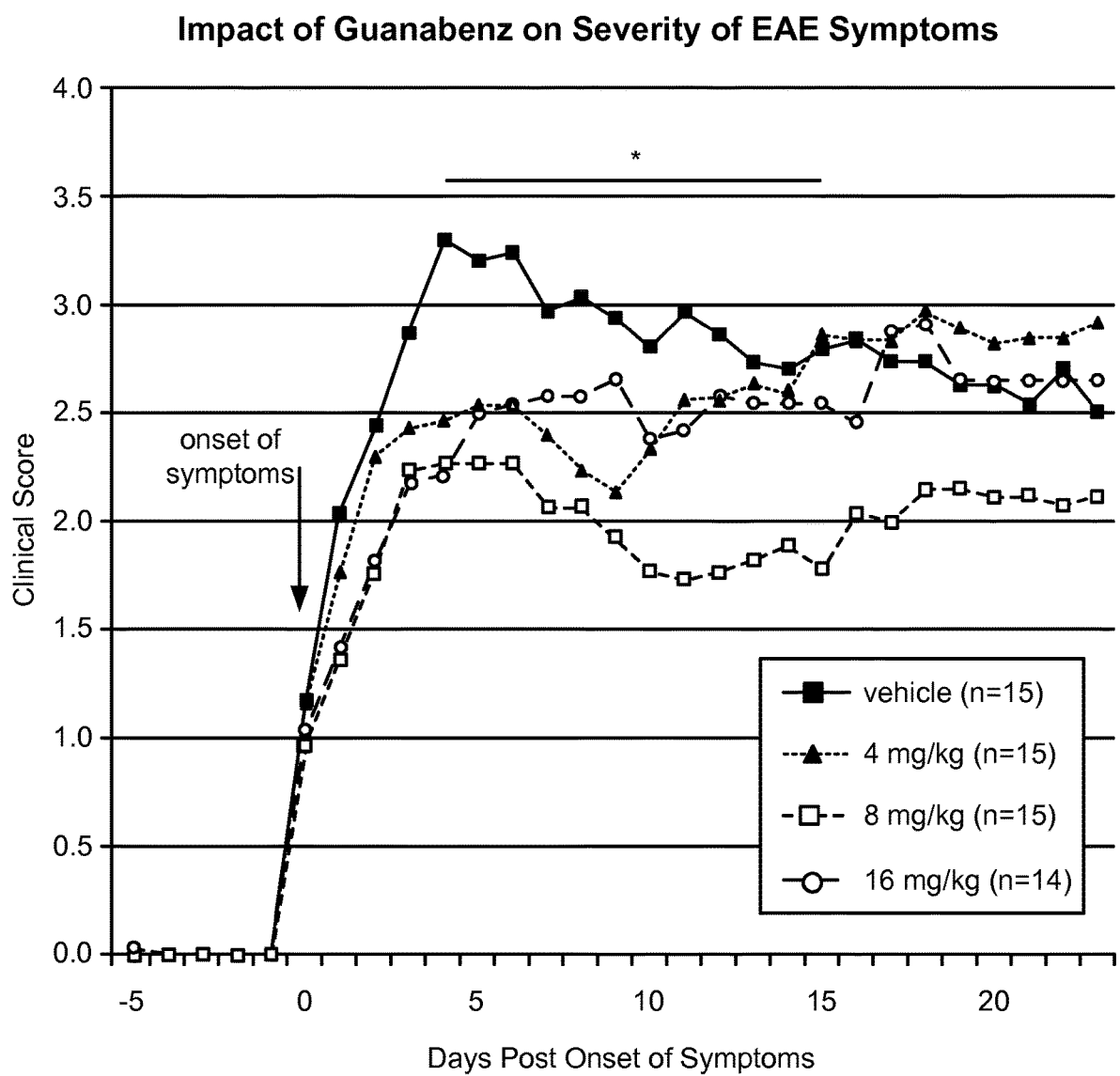
FIG. 6 depicts a plot of clinical scores over days post symptom onset. The mice were treated with 4-16 mg/kg/day of guanabenz or with control vehicle.

Example 5 guanabenz reduces symptom severity in an in vivo mouse model of chronic multiple sclerosis (FIG. 6). Data from Example 4 were rearranged such that clinical scores were plotted as a function of time, as measured by days post symptom onset. Vehicle-treated subjects exhibited clinical scores of about 3.0. Neither 4 mg/kg/day nor 16 mg/kg/day caused a significant reduction in clinical score, however, 8 mg/kg/day guanabenz significantly reduced symptom severity. Note: red bar indicates days during which *p≤0.05 compared to vehicle for the 8 mg/kg/day group.

Figure 7A:
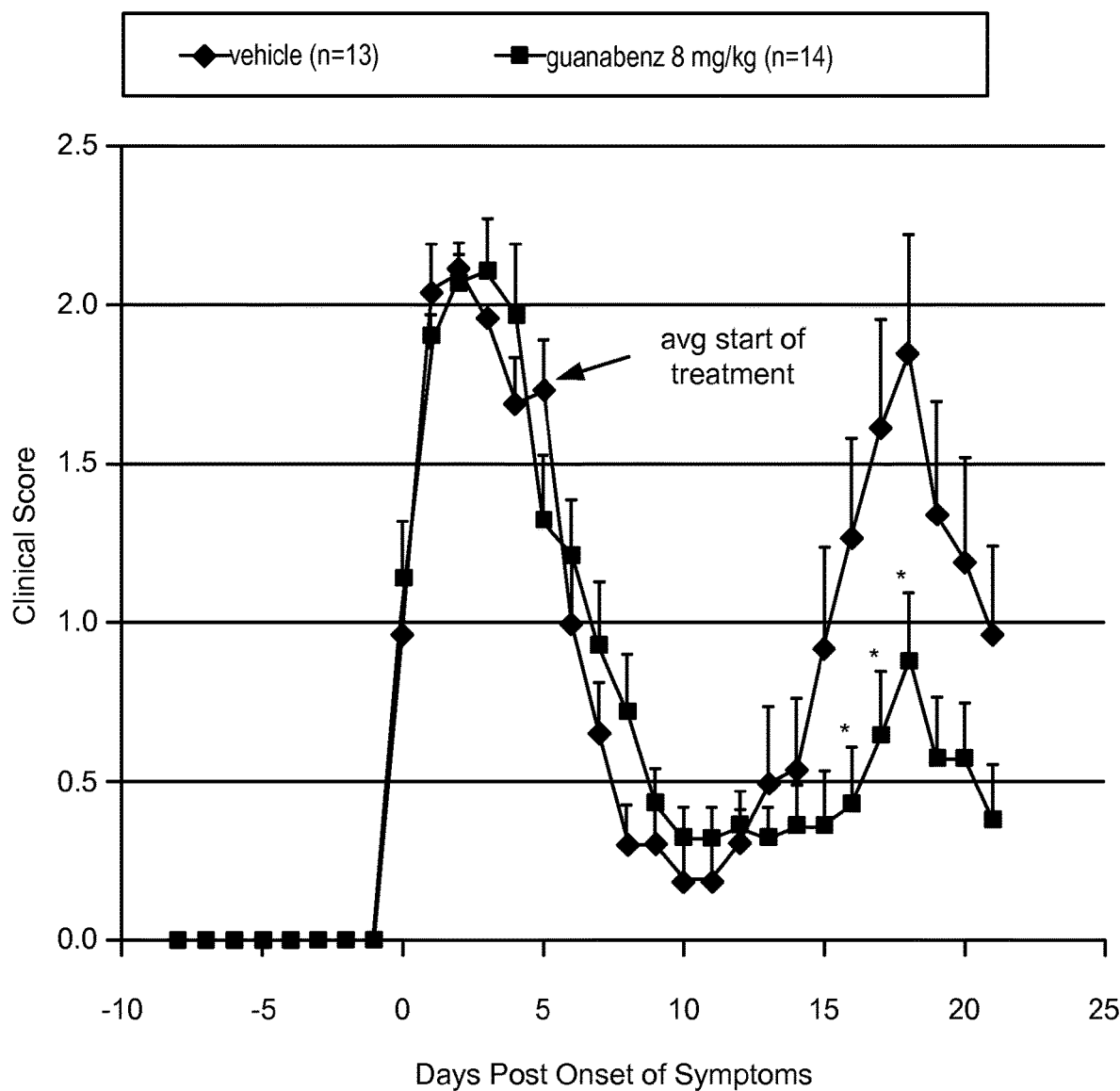
FIG. 7A depicts clinical scores over the course of remitting/relapsing EAE, a mouse model of remitting/relapsing multiple sclerosis. The mice were treated with 8 mg/kg/day guanabenz or control vehicle.

Example 6 guanabenz reduces the severity of symptom relapse in an in vivo mouse model of remitting/relapsing MS (FIG. 7A). Briefly, subcutaneous injections of 50 μg proteolipid protein (PLP) 139-151 peptide emulsified in complete Freund's adjuvant (BD Biosciences) supplemented with 200 μg of *Mycobacterium tuberculosis* (strain H37Ra; BD Biosciences) were injected into the lower flanks of 8 week old female SJL mice (Harlan Laboratories, Indianapolis, Ind.). Mice were monitored for clinical symptoms beginning post-immunization day 7 (PID 7) and scored daily as described above. Animals that did not achieve an acute phase (5 out of 50) were removed from the study. Mice were then treated IP with 8 mg/kg guanabenz or vehicle (sterile 0.9% NaCl) daily at the beginning of remission, defined as the second sequential day of reduced clinical score after the peak score of the acute phase. Mice that did not undergo a relapse phase (9 out of 22 vehicle-treated, 9 out of 23 guanabenz-treated) were removed from the study. Animals treated with 8 mg/kg guanabenz exhibited an average decrease in relapse severity of about 50%. Error bars represent mean±SEM for an N=13-14/group.

Figure 7B:
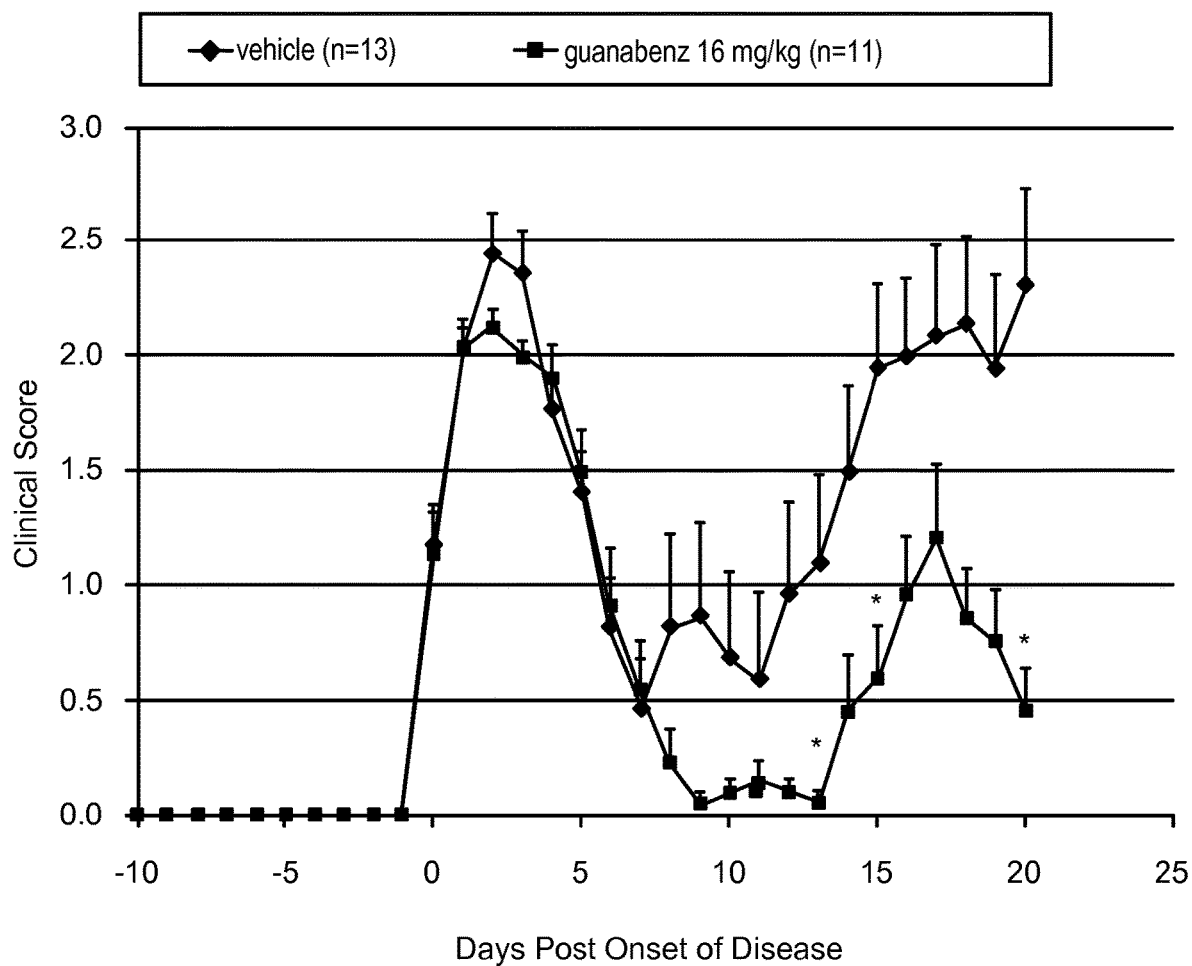
FIG. 7B depicts clinical scores over the course of remitting/relapsing EAE, a mouse model of remitting/relapsing multiple sclerosis. The mice were treated with 16 mg/kg/day guanabenz or control vehicle.

Example 7 higher doses of guanabenz also reduce symptom scores during the remission phase in an in vivo mouse model of remitting/relapsing MS (FIG. 7B). Briefly, SJL mice were exposed to $PLP_{139-151}$, monitored for clinical scores daily, and administered 16 mg/kg/day guanabenz as described herein. Upon onset of remission (defined as reduction of clinical score for at least two days after the peak score from the first, acute phase), animals were given daily IP injections of vehicle or guanabenz. Animals that exhibit relapse were assessed for severity of clinical scores during relapse. Animals treated with 16 mg/kg guanabenz exhibited an average decrease in relapse severity of about 40%. Furthermore, animals treated with 16 mg/kg/day guanabenz also exhibited a greater decrease in symptom severity during the remission phase, compared to vehicle-treated animals. N=11-13/group.

Figure 8:
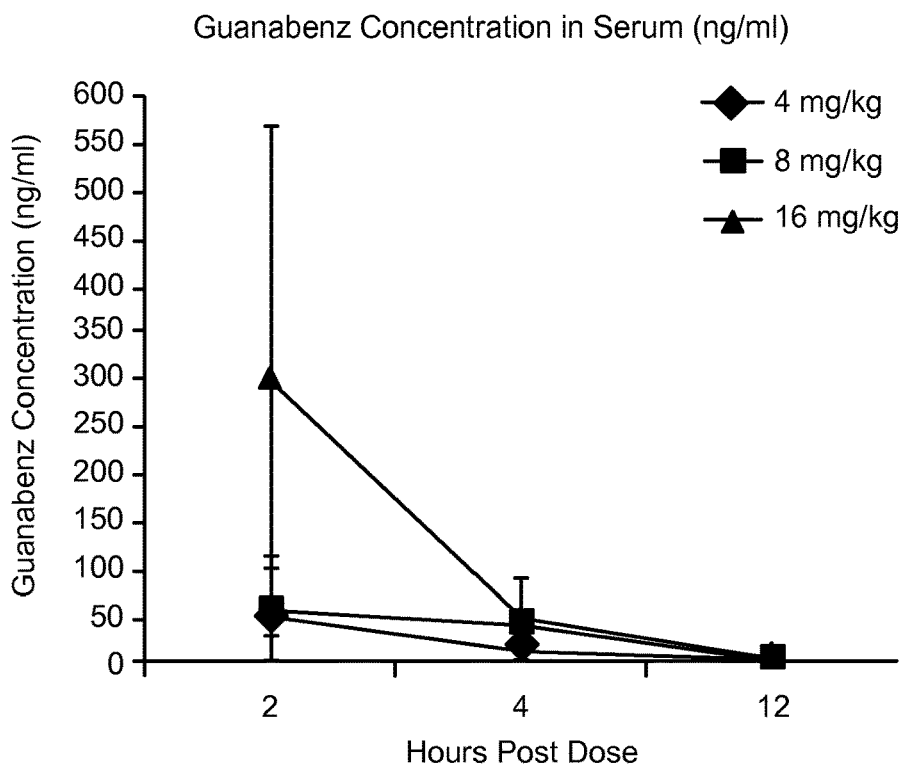
FIG. 8 depicts the time course of serum and brain concentrations of guanabenz, expressed as ng/ml or ng/g, in mice administered 4-16 mg/kg guanabenz daily after EAE induction.
Figure 8:
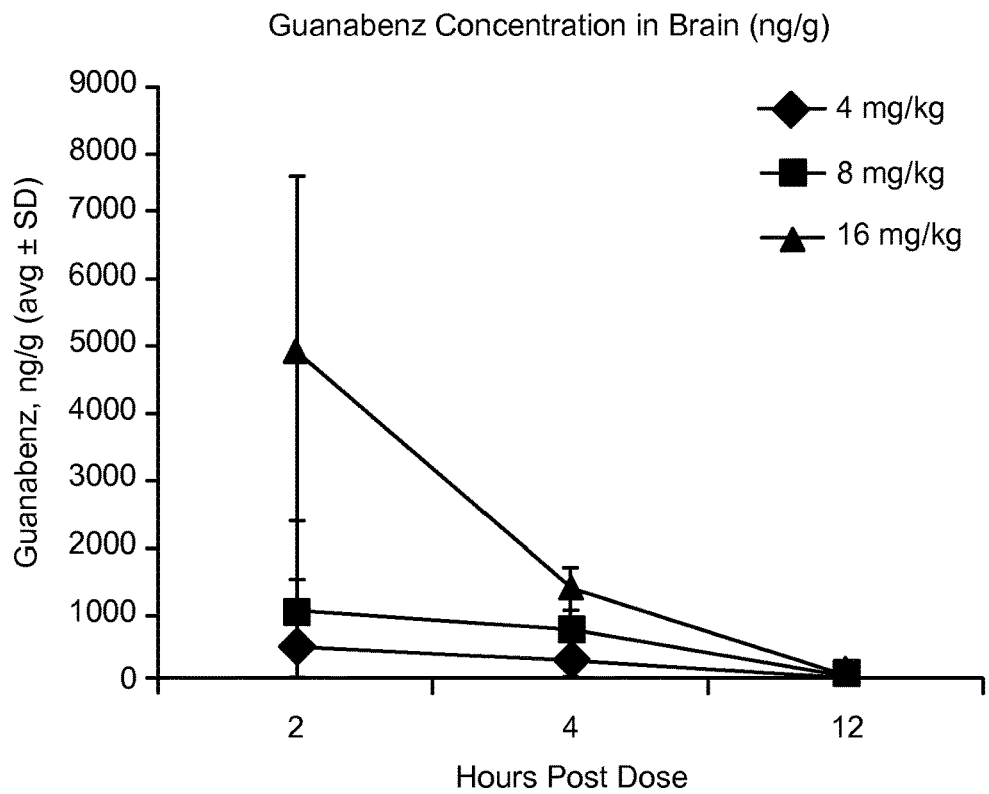
Figure 9:
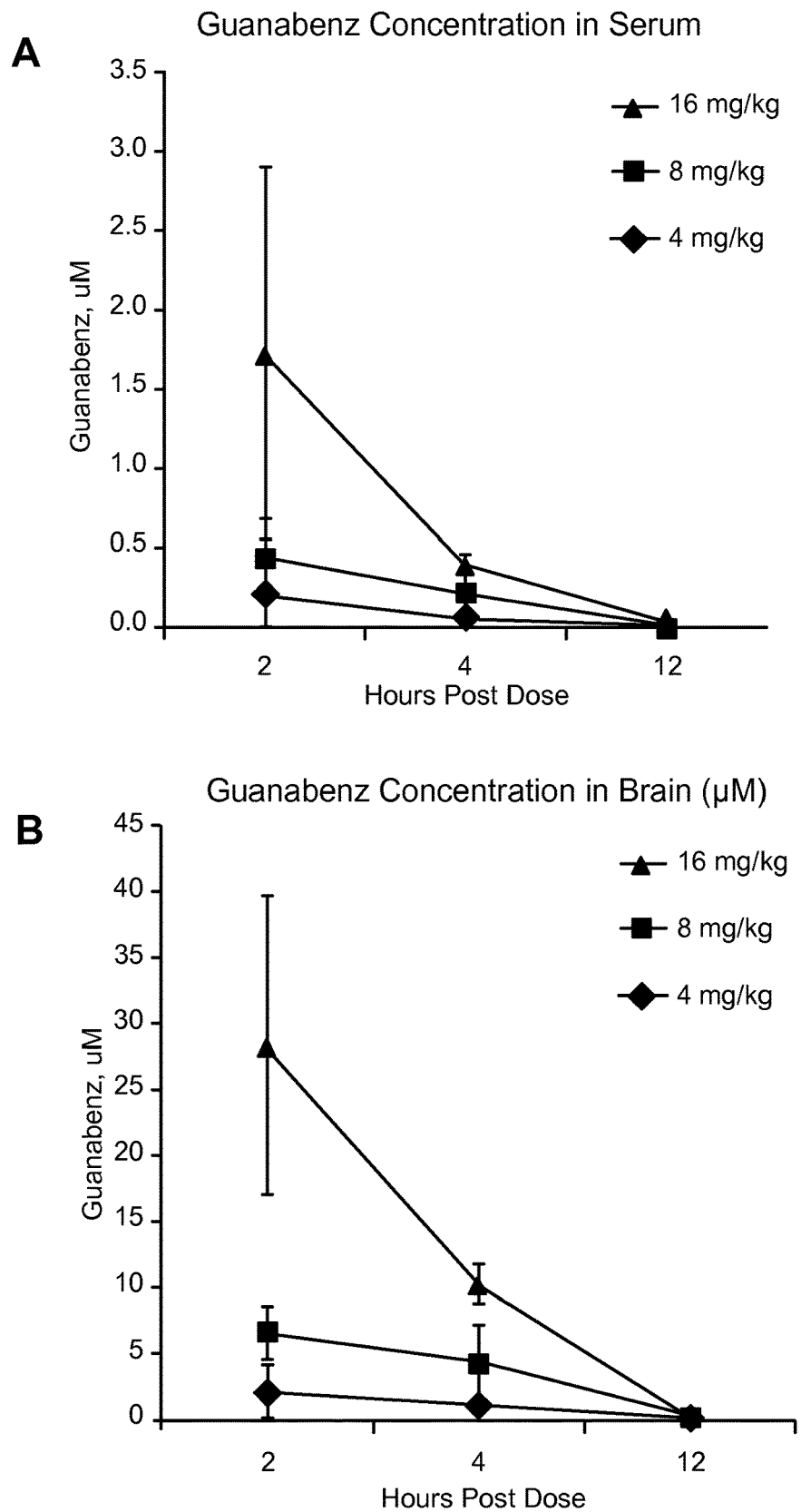
FIG. 9 depicts the time course of serum and brain concentrations of guanabenz, expressed in μM concentrations, in mice administered 4-16 mg/kg guanabenz daily after EAE induction.

Example 8 guanabenz doses used in the in vivo and in vitro studies described herein are comparable to doses used in humans (FIGS. 8, 9). C57Bl/6J females immunized with $MOG_{35-55}$-specific EAE as described above were treated daily IP with vehicle or 4, 8, or 16 mg/kg guanabenz diluted in sterile 0.9% NaCl from PID 7 to around PID 35. Mice were then given a final injection before serum was collected 2, 4, or 12 hours later via submandibular bleed. Immediately following blood draw, mice were perfused with 0.9% NaCl and their brains collected and weighed. Samples were then outsourced for analysis of guanabenz concentrations by HPLC-MS/MS. FIG. 8 depicts guanabenz concentrations in blood serum (A) and brain (B). Though guanabenz appears to be quickly cleared in both serum and brain in the mouse, the effective dose of 8 mg/kg appears to maintain a concentration of ~50 ng/ml in serum up to 4 hours after treatment (A). This concentration is comparable to that seen in human plasma up to 36 hours after patients were given a single typical dose of 32 mg of guanabenz (Meachem 1980, Clin Pharmacol Ther). This finding indicates that the dose found to be effective in alleviating and delaying onset of EAE symptoms in mice is comparable to a dosage that is known to be well-tolerated in humans. Guanabenz concentrations in brain tissue are roughly 16-20× higher than those in serum (B). Data represents mean±SD. FIG. 9 depicts the same data, with brain and serum concentrations expressed as μM values. Data depicted in FIGS. 2-3 demonstrated that, compared to IFN-γ-challenged controls, 2.5-5.0 μM guanabenz in cell culture and 2.5-10 μM guanabenz in cerebellar slice culture could significantly increase cell survival and inhibit hypomyelination, respectively. Comparison of these concentrations to those found in the serum (A) and particularly the brain tissue (B) of mice treated with guanabenz indicate that the effective in vivo and in vitro doses used are comparable. Data represents mean±SD.

Figure 10:
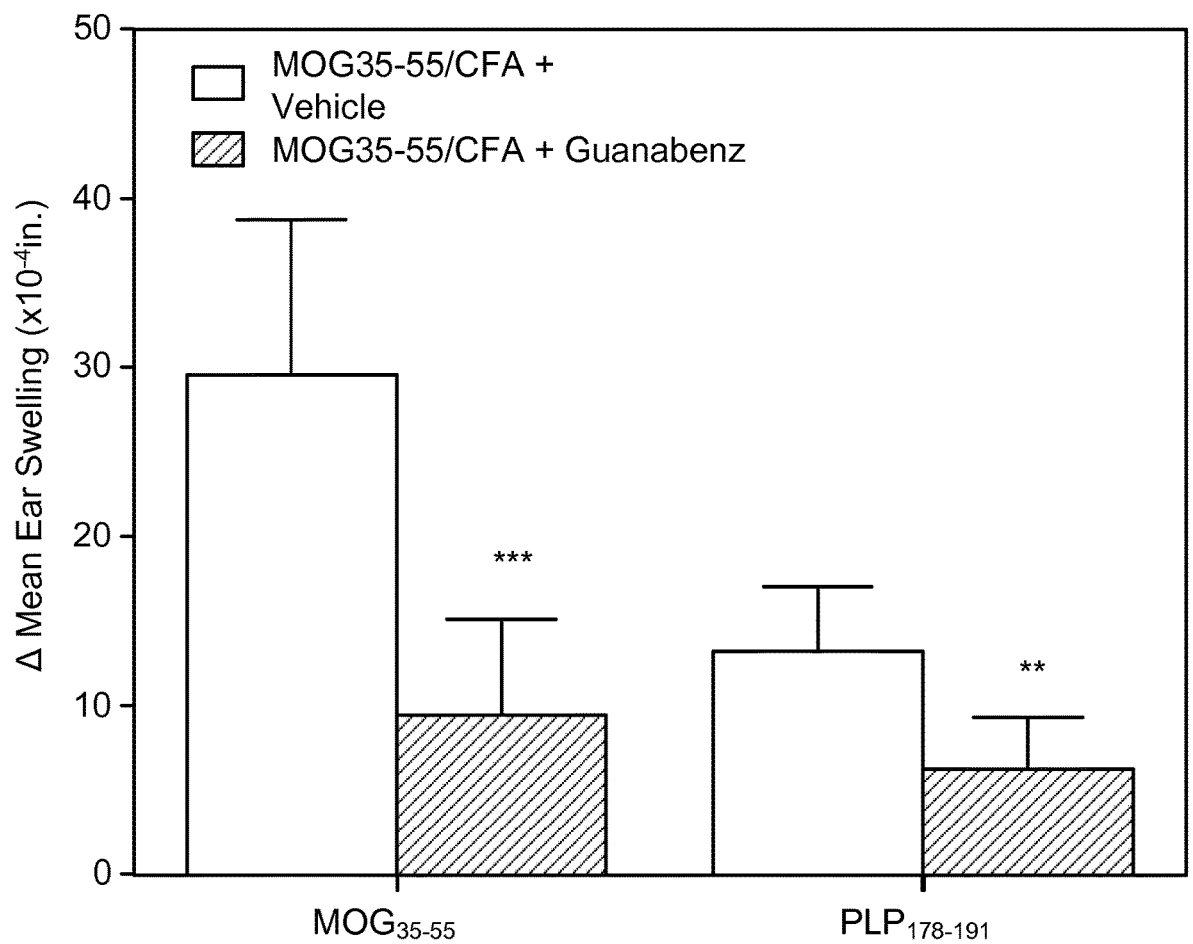
FIG. 10 depicts inflammatory ear-swelling response to a local injection of $MOG_{35-55}$, the antigen used to induce EAE. The mice were treated with 8 mg/kg/day guanabenz or control vehicle.

Example 9 guanabenz reduces inflammatory immune responses to myelin proteins in an in vivo mouse model of EAE (FIG. 10). Mice immunized with $MOG_{35-55}$-specific EAE (as described herein) were treated with vehicle or 8 mg/kg guanabenz daily IP from PID 7 to PID 19. On PID 17, mice were challenged via a single injection of 10 μg of $MOG_{35-55}$ peptide solubilized in 10 μl of 1×PBS in the dorsal surface of the left ear and 10 μg of $PLP_{178-191}$ peptide in 10 μl 1×PBS in the right ear. Response was assessed 48 hours later by measuring ear thickness. 8 mg/kg guanabenz decreased mean ear swelling to about one-third of vehicle-administered subjects. N=8-9/group. (p<0.005, *p<0.0005)

Figure 11:
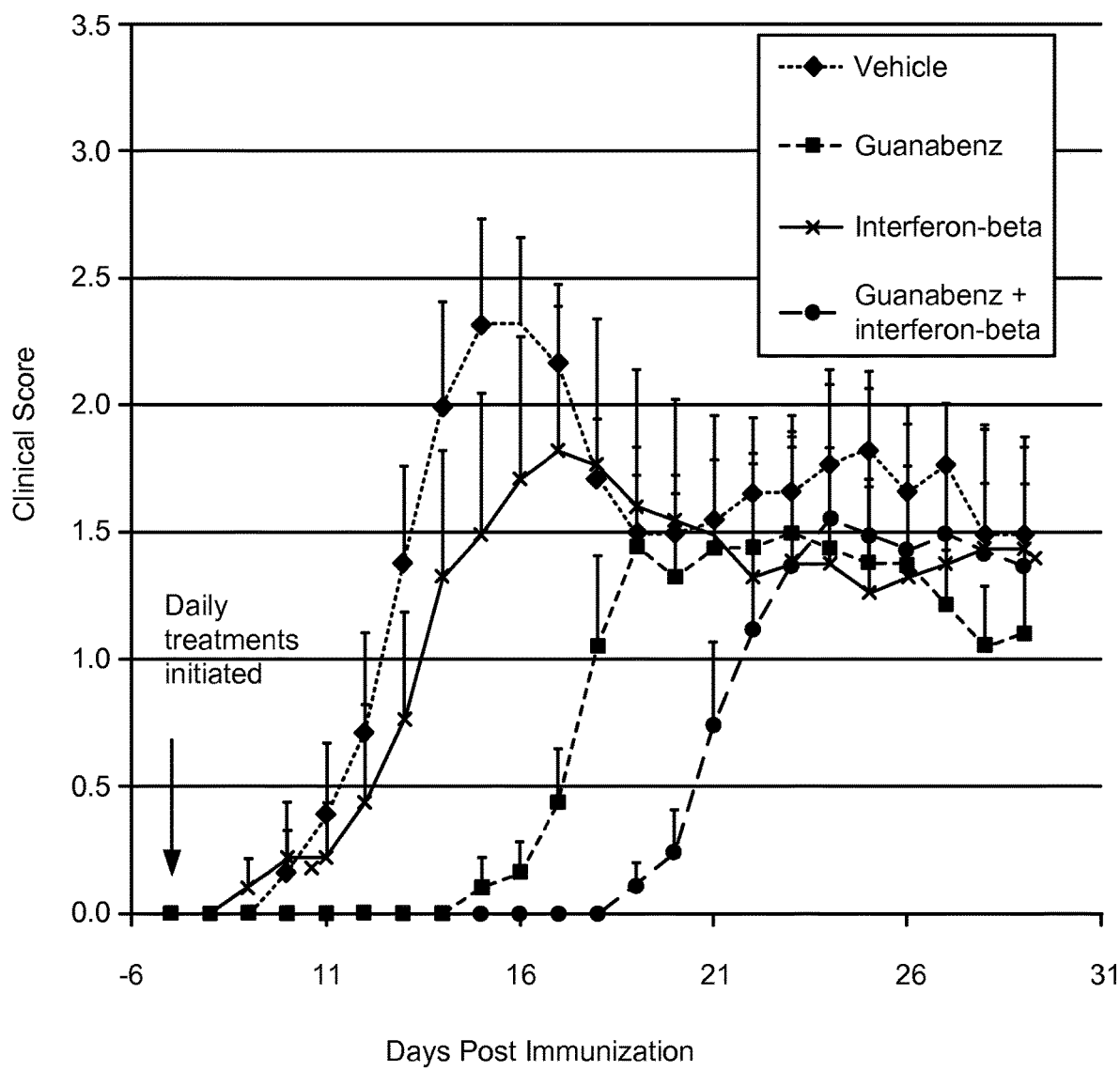
FIG. 11 depicts effects of guanabenz/interferon co-administration on clinical symptoms in chronic EAE mice. The mice were treated with control vehicle, 8 mg/kg/day guanabenz, 5000 U/day interferon, or a combination of guanabenz and interferon.

Example 10 co-administration of guanabenz and interferon delays onset of clinical symptoms in chronic EAE mice to a greater extent than either guanabenz alone or interferon alone (FIG. 11). Eight week old C57BL/6J female mice were immunized with $MOG_{35-55}$/CFA to induce chronic EAE. Vehicle (saline), guanabenz (8 mg/kg), interferon-beta (5,000 U/day/mouse) or combined guanabenz/interferon-beta treatments were administered daily beginning post immunization day 7. Mice were scored daily for clinical symptoms (0=healthy, 1=flaccid tail, 2=ataxia and/or paresis of hindlimbs, 3=paralysis of hindlimbs and/or paresis of forelimbs, 4=tetraparalysis, 5=moribund or death). Treatment with interferon alone did not significantly delay onset of clinical symptoms. Onset of clinical symptoms began at approximately day 12 in saline-treated mice and at approximately day 13 in mice treated with interferon alone. Onset of clinical symptoms began at approximately day 18 in mice treated with guanabenz alone. Onset of clinical symptoms was further delayed in mice treated with guanabenz and interferon, beginning at approximately day 22 for the co-administered mice. These results indicate a synergistic effect of guanabenz and interferon for delaying onset of clinical symptoms of a demyelinating disorder. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a demyelinating disorder in a subject in need thereof, comprising the step of administering to the subject in need thereof an effective amount of a compound of Formula I:

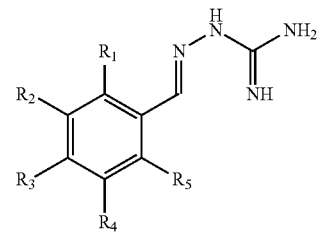

or a derivative or pharmaceutically acceptable salt thereof, wherein $R_1$, $R_2$, $R_3$, $R_4$, and $R_5$ are independently hydrogen, deuterium, halogen, haloalkyl, alkyl, alkoxy, hydroxyl, aryl, or aryloxy, thereby treating a demyelinating disorder in said subject.

2. The method of claim 1, wherein $R_1$ and $R_5$ are not hydrogen and/or wherein $R_1$ and $R_5$ are halogen.

3. The method of claim 1, wherein the compound of Formula I is of Formula II or pharmaceutically acceptable salt thereof:

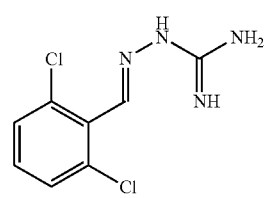

Formula II

4. The method of claim 1, wherein the demyelinating disorder is selected from the group consisting of: multiple sclerosis, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, Guillain-Barré Syndrome, central pontine myelinolysis, diffuse white matter injury, leukodystrophy, and Charcot Marie Tooth Disease.

5. The method of claim 1, wherein treating comprises treating a symptom of a demyelinating disorder, wherein the symptom is selected from the group consisting of: fatigue, somatosensory dysfunction, tingling, pain, numbness, balance problems, problems with walking, changes in vision, depression, emotional changes, mood swings, impaired cognition, muscle dysfunction, impaired muscle coordination, sexual impairment, speech impairment, swallowing impairment, bladder dysfunction, bowel dysfunction.

6. The method of claim 1, wherein about 1 mg to about 64 mg of the compound is administered to the subject.

7. The method of claim 1, wherein the compound is administered orally.

8. The method of claim 1, wherein the administration of the compound is combined with one or more of glatiramer acetate, dimethyl fumerate (BG-12), fingolimod (FTY720), interferon beta-1a, interferon beta-1b, mitoxantrone, natalizumab, dalfampridine, teriflunomide, and/or daclizumab.

9. The method of claim 1, wherein the compound of Formula I is guanabenz.

10. The method of claim 9, wherein about 64 mg/day of said guanabenz is administered to said subject.

11. The method of claim 1, wherein the compound of Formula I is:

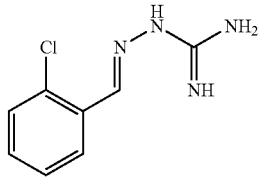 [SMILES: N=C(N)N/N=C/c1ccccc1Cl]

or a pharmaceutically acceptable salt thereof.

12. The method of claim 1, wherein the size and/or number of white matter plaques and/or lesions is reduced.

13. The method of claim 1, wherein treating comprises protecting brain cells from inflammation.

14. The method of claim 1, wherein the administration of the compound is combined with glatiramer acetate.

15. A method of treating multiple sclerosis in a subject in need thereof, comprising the step of administering to the subject in need thereof an effective amount of

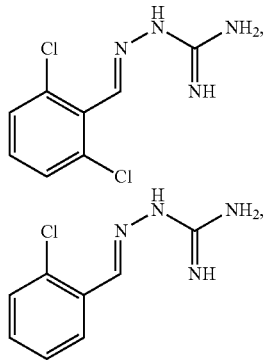

or a pharmaceutically acceptable salt thereof.

16. A method for inhibiting hypomyelination in a subject in need thereof, comprising the step of administering to the subject in need thereof an effective amount of

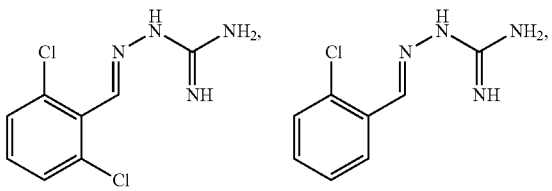 [SMILES: N=C(N)N/N=C/c1c(Cl)cccc1Cl ; N=C(N)N/N=C/c1ccccc1Cl]

or a pharmaceutically acceptable salt thereof.

17. The method of claim 16, wherein the subject has or has been diagnosed with multiple sclerosis.

* * * * *